(12) United States Patent
Khusial et al.

(10) Patent No.: US 9,675,543 B2
(45) Date of Patent: *Jun. 13, 2017

(54) METHOD OF IMPROVING AGING APPEARANCE OF SKIN BY MODULATION OF WIPI-1

(71) Applicant: Avon Products, Inc., Suffern, NY (US)

(72) Inventors: Permanan Raaj Khusial, Highland Mills, NY (US); Uma Santhanam, Tenafly, NJ (US); John W. Lyga, Basking Ridge, NJ (US)

(73) Assignee: Avon Products, Inc., Rye, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/661,061

(22) Filed: Mar. 18, 2015

(65) Prior Publication Data

US 2015/0190339 A1   Jul. 9, 2015

Related U.S. Application Data

(62) Division of application No. 14/055,037, filed on Oct. 16, 2013, now Pat. No. 9,238,000.

(60) Provisional application No. 61/735,649, filed on Dec. 11, 2012.

(51) Int. Cl.
| | |
|---|---|
| *A61K 8/97* | (2017.01) |
| *A61K 8/49* | (2006.01) |
| *A61Q 19/08* | (2006.01) |
| *A61K 8/67* | (2006.01) |
| *C12Q 1/68* | (2006.01) |

(52) U.S. Cl.
CPC ............... *A61K 8/97* (2013.01); *A61K 8/49* (2013.01); *A61K 8/671* (2013.01); *A61Q 19/08* (2013.01); *C12Q 1/6876* (2013.01); *C12Q 1/6883* (2013.01); *C12Q 2600/136* (2013.01); *C12Q 2600/148* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 4,322,438 A | 3/1982 | Peck | |
| 6,146,640 A | 11/2000 | Dyke | |
| 7,618,662 B2 | 11/2009 | Hines et al. | |
| 8,394,427 B2 | 3/2013 | Zheng et al. | |
| 8,455,518 B2 | 6/2013 | Khusial et al. | |
| 8,512,764 B2 * | 8/2013 | Paufique | A61K 8/97 424/195.16 |
| 8,686,013 B2 * | 4/2014 | Lyga | A61K 8/49 514/374 |
| 8,709,507 B2 * | 4/2014 | Chen | A61K 8/97 424/725 |
| 8,771,758 B2 * | 7/2014 | Ptchelintsev | A61Q 19/08 424/47 |
| 8,815,265 B2 | 8/2014 | Ptchelintsev et al. | |
| 8,865,740 B2 | 10/2014 | Khusial et al. | |
| 8,927,517 B2 | 1/2015 | Murase et al. | |
| 9,034,396 B2 * | 5/2015 | Zheng | A61K 8/97 424/725 |
| 9,056,842 B2 * | 6/2015 | Lyga | A61K 8/49 |
| 9,132,294 B2 * | 9/2015 | Zheng | A61K 8/466 |
| 9,186,316 B2 * | 11/2015 | Khusial | A61K 8/97 |
| 9,238,000 B2 * | 1/2016 | Khusial | A61K 8/97 |
| 2003/0207818 A1 | 11/2003 | Jia et al. | |
| 2005/0136028 A1 | 6/2005 | Ptchelintsev | |
| 2006/0024390 A1 | 2/2006 | Schauss et al. | |
| 2006/0134231 A1 | 6/2006 | Hines et al. | |
| 2007/0224272 A1 | 9/2007 | Touitou | |
| 2008/0274453 A1 | 11/2008 | Hageman | |
| 2010/0166677 A1 | 7/2010 | Ptchelintsev | |
| 2012/0003331 A1 | 1/2012 | Ptchelintsev et al. | |
| 2012/0003332 A1 | 1/2012 | Zheng et al. | |
| 2012/0225092 A1 | 9/2012 | Paufique | |
| 2012/0282194 A1 | 11/2012 | Florence et al. | |
| 2013/0052288 A1 * | 2/2013 | Leeson | A61K 8/97 424/757 |
| 2013/0053423 A1 * | 2/2013 | Lyga | A61K 8/49 514/374 |
| 2013/0102606 A1 * | 4/2013 | Hwang | A61K 8/4946 514/236.5 |
| 2013/0149268 A1 * | 6/2013 | Chen | A61K 8/97 424/62 |
| 2013/0149397 A1 * | 6/2013 | Chen | A61Q 19/08 424/725 |
| 2016/0089327 A1 * | 3/2016 | Khusial | A61K 8/97 424/757 |

FOREIGN PATENT DOCUMENTS

| | | |
|---|---|---|
| CN | 101039579 A | 9/2007 |
| CN | 101559033 A | 10/2009 |
| JP | 2000128730 A | 5/2000 |
| JP | 2002087973 A | 3/2002 |
| JP | 2006069954 A | 3/2006 |

(Continued)

OTHER PUBLICATIONS

Tiliacora Triandra Fresh 200 Leaves, 20 pages (2015).
Keratinocytes, 1 page (2015).
Kang et al., "Topical N-Acetyl Cysteine and Genistein Prevent Ultraviolet-Light-Induced Signaling That Leads to Photoaginig in Human Skin in vivo," The Society for Investigative Dermatology, Inc., vol. 120, No. 5, pp. 835-841 (2003).
Nanasombat et al., "Antimicrobial, antioxidant and anticancer activities of Thai local vegetables," Journal of Medicinal Plants Research, vol. 3, No. 5, pp. 443-449 (2009).
Singthong et al., "Extraction and physicochemical characterisation of polysaccharide gum from Yanang (*Tiliacora triandra*) leaves," Food Chemistry, vol. 114, pp. 1301-1307 (2009).

(Continued)

*Primary Examiner* — Ralph Gitomer
(74) *Attorney, Agent, or Firm* — Brian P. McCloskey

(57) ABSTRACT

Methods of using WIPI-1 to impart anti-aging benefits to the skin and/or improve skin conditions resulting from reduced autophagy activity.

5 Claims, 6 Drawing Sheets

(56) References Cited

FOREIGN PATENT DOCUMENTS

| | | | |
|---|---|---|---|
| JP | 2010090069 A | 4/2010 | |
| WO | 2006068778 A2 | 6/2006 | |
| WO | 2007093839 A1 | 8/2007 | |
| WO | 2009018493 A1 | 2/2009 | |
| WO | 2009134404 A2 | 11/2009 | |
| WO | 2012002950 A1 | 1/2012 | |
| WO | 2012005872 A1 | 1/2012 | |
| WO | 2012005876 A1 | 1/2012 | |
| WO | 2012005876 A2 | 1/2012 | |
| WO | 2013028267 A2 | 2/2013 | |
| WO | 2013090228 A2 | 6/2013 | |

OTHER PUBLICATIONS

Choi, Eun-Mi et al., "Screening of Indonesian medicinal plants for inhibitor activity on nitric oxide production of RAW264.7 cells and antioxidant activity," Fitoterapia, vol. 76, pp. 194-203 (2005).

Fujimoto, Norihiro et al., "Expression of microfibril-associated glycoprotein-1 (MAGP-1) in human epidermal keratinocytes," Arch. Dermatol. Res. vol. 292, pp. 21-26 (2000).

Jothi, G. J. et al., "Glimpses of Tribal Botanical Knowledge of Tirunelveli Hills, Western Ghats, India," Ethnobotanical Leaflets, vol. 12, pp. 118-126 (2008).

Micor, Jose Rene L. et al., "Biological Activity of Bignay [*Antidesma bunius* (L.) Spreng] Crude Extract in Artemia salina," J. Med. Sci., vol. 5, No. 3, pp. 195-198 (2005).

Mintel, "Treatment Cream," Database GNPD [online], database accession No. 1646948 (2011).

Tatano, Yutaka et al., "Significant Decrease in Tropoelastin Gene Expression in fibroblasts from a Japanese Costello Syndrome Patient with Impaired Elastogenesis and Enhanced Proliferation," J. Biochem., vol. 140, pp. 193-200 (2000).

Durden et al., "Qualitative and Quantitative Mass Spectrometry of some Noncatecholic Biogenic Amines and Related Compounds as their Dansyl Derivatives," Biomedical Mass Spectrometry, pp. 83-95 (1974).

http://www.emedicinehealth.com/wrinkles/article_em.htm (2013).

Ho et al., WIPI1 Coordinates Melanogenic Gene Transcription and Melanosome Formation Via TORC1 Inhibition, Journal of Biological Chemistry, vol. 286, No. 14, pp. 12509-12523.

Weinbaum et al., "Deficiency in Microfibril-associated Glycoprotein-1 Leads to Complex Phenotypes in Multiple Drgan Systems," Journal of Biological Chemistry, vol. 283, No. 37, pp. 25533-25543 (2008).

Revilla, Eugenio et al., "Comparison of Several Procedures Used for the Extraction of Anthocyanins from Red Grapes," J. Agric. Food Chem., vol. 46, pp. 4592-4597 (1998).

Proikas-Cezanne et al. WIPI-1a (WIPI49), a member of the novel 7-bladed WIPI protein family, is aberrantly expressed in human cancer and is linked to starvation-induced authophagy. Oncogene 23(58): 9314-9325, 2004.

Cuervo et al. Autophagy and Aging: The Importance of Maintaining "Clean" Cells Autophagy 1(3): 131-140, 2005.

U.S. Appl. No. 12/345,707, filed Dec. 30, 2008, Ptchelinstev.
U.S. Appl. No. 12/813,732, filed Jun. 11, 2010, Ptchelinstev.
U.S. Appl. No. 14/331,638, filed Jul. 15, 2014, Ptchelinstev et al.
U.S. Appl. No. 13/158,947, filed Jun. 13, 2011, Zheng, Qian et al.
U.S. Appl. No. 13/305,779, filed Nov. 29, 2011, Zheng, Qian et al.
U.S. Appl. No. 14/284,869, filed May 22, 2014, Ptchelintsev, Dmitri.
U.S. Appl. No. 14/066,862, filed Oct. 30, 2013, Lyga et al.
U.S. Appl. No. 13/710,617, filed Dec. 11, 2012, Zheng et al.
U.S. Appl. No. 14/379,544, filed Aug. 19, 2014, Mei et al.
U.S. Appl. No. 12/648,581, filed Dec. 29, 2009, Lyga, John W. et al.
U.S. Appl. No. 13/602,557, filed Sep. 4, 2012, Zheng, Qian et al.
U.S. Appl. No. 13/216,626, filed Aug. 24, 2011, Thorn Leeson, Daniel.
U.S. Appl. No. 13/710,536, filed Dec. 11, 2012, Hwang, Cheng et al.
U.S. Appl. No. 13/814,383, filed Feb. 5, 2013, Zheng, Qian et al.
U.S. Appl. No. 13/293,109, filed Mar. 11, 2013, Zheng, Qian et al.
U.S. Appl. No. 14/055,037, filed Oct. 16, 2013, Khusial et al.

* cited by examiner

METHOD OF IMPROVING AGING APPEARANCE OF SKIN BY MODULATION OF WIPI-1

RELATED APPLICATIONS

This application claims priority to and is a divisional application of U.S. Nonprovisional patent application Ser. No. 14/055,037, filed on Oct. 16, 2013, now U.S. Pat. No. 9,238,000, which itself claims priority to U.S. Provisional Patent Application Ser. No. 61/735,649, filed on Dec. 11, 2012. The entirety of each of the aforementioned applications is hereby incorporated by reference in its entirety for all purposes.

FIELD OF INVENTION

The present invention relates generally to compositions for topical application to the skin which comprise at least one WIPI-1 agonist and the use of such compositions to provide benefits to the skin, in particular, improving autophagy activity within skin cells and in a further embodiment improving the condition and appearance of chronologically or photo aged skin.

BACKGROUND OF THE INVENTION

Consumers are increasingly interested in cosmetics that treat, mitigate, or delay the signs of aging or aged skin. During the aging process, the complexion of the skin, i.e., the color and appearance of the skin, deteriorates slowly from aging and/or exposure to sunlight. Dermatological signs of chronologically, hormonally-aged, or photo-aged skin manifest themselves in lines and wrinkles, sagging, dullness, discoloration, uneven tone, and/or rough texture. Further, aged skin lacks strength and elasticity and is therefore fragile. The cosmetics industry is actively pursuing products that may be used to reduce signs of aging or aged skin (anti-aging compounds) and thereby provide anti-wrinkle, rejuvenating, and skin coloring benefits.

Autophagy is a catabolic process that helps in maintaining an unequivocal balance between the synthesis and degradation of proteins, and subsequent recycling of cellular products. Autophagy is a mechanism for recycling and detoxifying cellular components and organelles, i.e., it gets rid of bulky cell components such as damaged organelles (e.g. mitochondria) and protein aggregates. In particular, autophagy makes it possible to regulate, repair and eliminate proteins with a long service life in skin cells (e.g., fibroblasts, melanocytes, and/or keratinocytes), thus ensuring a control during differentiation and aging of human skin.

On the cellular plane, the autophagy mechanism comprises four stages: (1) initiation, (2) formation of an initial vacuole ("autophagosome"), which sequesters the cytoplasmic material, (3) the maturation of the autophagosome into a degradative vacuole, and (4) fusion with the lysosome until the degradation of the sequestered material is achieved. If this process breaks down or slows down, damaged organelles and proteins will accumulate within the cell interfering with normal cellular functions, especially protein synthesis, and ultimately cell viability.

WIPI-1 (Atg-18) is a member of the WD40 repeat proteins, and has a 7-bladed propeller structure that allows reversible protein-protein interactions. WIPI-1 also contains a conserved motif for interaction with phospholipids. These structural features make WIPI-1 a good candidate to be a part of the autophagasome vacuole, and recent studies have confirmed its involvement in autophagy in human cells. Autophagy 7:3, 279-296; March 2011; © 2011 Landes Bioscience and Anne Simonsen and Sharon A. Tooze, "Coordination of membrane events during autophagy by multiple class III PI3-kinase complexes," J. Cell Biol. Vol. 186 No. 6 773-782. It has been demonstrated that endogenous WIPI-1 protein co-localizes with the autophagosomal marker LC3 at punctate cytoplasmic structures in human cells to initiate the formation of the vacuole. Proikas-Cezanne et al., Human *WIPI-1 puncta-formation: A novel assay to assess mammalian autophagy*, FEBS Letters 581 (2007) 3396-3404.

U.S. Patent Publication No. 20120225092 entitled Cosmetic Use of Skin Cell Autophagy Activators discusses the use of various compounds to increase autophagy within skin cells through the up-regulation of the ATG5-12 and MAP-LC3 protein complexes. Also, Hu et al., WIPI1 Coordinates Melanogenic Gene Transcription and Melanosome Formation Via TORC1 Inhibition, *Journal of Biological Chemistry*, vol. 286, No. 14, pp. 12509-12523 (2011), discloses WIPI1's influence upon the regulation of melanosome formation.

Thus, a need remains for cosmetic compositions which reduce the manifestations of skin aging associated with reduced autophagy activity within skin cells. It is therefore an object of the invention to provide new compositions and methods for increasing, maintaining and/or restoring autophagy activity levels within skin cells. It is a further object of the invention to improve the overall appearance of skin, including treating, reversing, and/or preventing signs of skin aging or damage, such as wrinkles, fine lines, discoloration, loss of tone, loss of elasticity, thinning, etc. by up-regulating WIPI-1 within skin cells.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

SUMMARY OF THE INVENTION

The current invention relates to a method for improving the appearance of skin affected by chronological or photo aging by topically applying thereto an effective amount of at least one WIPI-1 agonist, in a cosmetically acceptable vehicle for a time sufficient to achieve an improvement in the autophagy activity of said skin.

Autophagy activity slows down as cells age either due to intrinsic factors or the influence of photo-aging (UV exposure). WIPI-1 expression is impaired by photo-aging as well. The resulting impairment in autophagy activity leads to accumulation of damaged cellular components in the cells which in turn lead to improper cellular functioning, including protein synthesis. This impairment in skin cell autophagy activity may translate into an exacerbation of manifestations of aging within skin cells such as an increase in morphological changes and cell body collapse within dermal fibroblasts; reduced and/or inconsistent melanin production by melanocytes; an increase in the turnover period and/or reduction in structural integrity of keratinocytes within the epidermis. Ultimately, these effects on skin cells exacerbate the appearance of fine lines, wrinkles, and/or discoloration, as well as the impair the structural integrity of the skin, i.e., inelastic, thin, and permeable skin.

In one embodiment, the current invention encompasses a method for improving the aesthetic appearance of skin affected by aging resulting from reduced autophagy activity within skin cells comprising topically applying thereto an effective amount of at least one WIPI-1 agonist, in a cosmetically acceptable vehicle for a time sufficient to achieve an improvement in the appearance of said skin.

In another embodiment, the current invention encompasses a method wherein aging may be due to chronological, hormonal, or environmental effects.

In a further method in accordance with the current invention, the improvement in aesthetic appearance is selected from:

(a) treatment, reduction, and/or prevention of fine lines or wrinkles,
(b) reduction of skin pore size,
(c) improvement in skin thickness, plumpness, and/or tautness;
(d) improvement in skin suppleness and/or softness;
(e) improvement in skin tone, radiance, and/or clarity;
(f) improvement in procollagen and/or collagen production;
(g) improvement in maintenance and remodeling of elastin;
(h) improvement in skin texture and/or promotion of re-texturization;
(i) improvement in skin barrier repair and/or function;
(j) improvement in appearance of skin contours;
(k) restoration of skin luster and/or brightness;
(l) replenishment of essential nutrients and/or constituents in the skin;
(m) improvement of skin appearance decreased by aging and/or menopause;
(n) improvement in skin moisturization and/or hydration;
(o) increase in and/or preventing loss of skin elasticity and/or resiliency;
(p) treatment, reduction, and/or prevention of skin sagging;
(q) treatment, reduction, and/or prevention of discoloration of skin; and any combination thereof.

In yet another embodiment, the improvement in aesthetic appearance may be detoxifying the skin.

In another embodiment, the current invention encompasses the method wherein the skin is sensitive skin.

In another embodiment, the current invention encompasses the method wherein the composition is topically applied at least once daily for at least one week.

In another embodiment of the method of the current invention, the WIPI-1 agonist may be present in an amount about 0.0001 wt % to about 90 wt % based on the total weight of the composition. In a further embodiment, the WIPI-1 agonist is present in an amount of from about 0.01 wt % to about 10 wt % of the total weight of the composition.

In another embodiment, the current invention encompasses the method in which the WIPI-1 agonist may be:

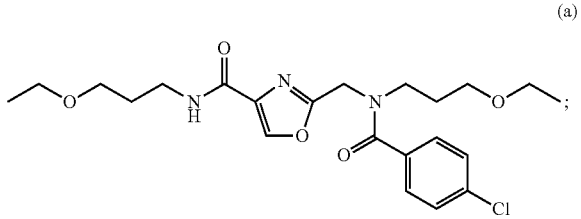

(a)

(b) an extract of *Archidendron clyperia;*
(c) an extract of *Ixora chinensis;*
(d) an extract of *Maesa japonica;*
(e) an extract of *Serrissa japonica;*
(f) an extract of *Stephanotis jasminoides;*
(g) an extract of *Tiliacora triandra;* or any combinations thereof.

In a further embodiment, the WIPI-1 agonist is not an extract of *Tiliacora triandra, Ixora chinensis,* or *Archidendron clyperia.*

In another embodiment, the current invention encompasses the method wherein the improvement of the skin is due to an increase in autophagy activity within skin cells. In yet another embodiment, the increase in autophagy activity within skin cells is about 20%.

In another embodiment, the current invention encompasses a method where the skin cells comprise fibroblasts or keratinocytes.

In another embodiment, the current invention encompasses a method where the WIPI-1 agonist is used in combination with a retinoid.

In another embodiment, the current invention encompasses a method for improving the appearance of skin having reduced autophagy activity within its constituent skin cells by topically applying thereto an effective amount of at least one WIPI-1 agonist, in a cosmetically acceptable vehicle for a time sufficient to modulate WIPI-1 mediated autophagy activity. In a further embodiment, the constituent skin cells comprise fibroblasts or keratinocytes.

In another embodiment, the current invention encompasses a method where the WIPI-1 agonist may be:

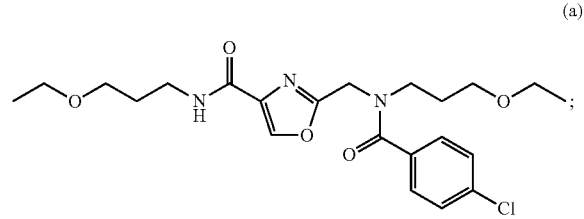 [SMILES: CCOCCCNC(=O)c1coc(CN(CCCOCC)C(=O)c2ccc(Cl)cc2)n1]

(a)

(b) an extract of *Archidendron clyperia;*
(c) an extract of *Ixora chinensis;*
(d) an extract of *Maesa japonica;*
(e) an extract of *Serrissa japonica;*
(f) an extract of *Stephanotis jasminoides;*
(g) an extract of *Tiliacora triandra;* or any combinations thereof.

In yet another embodiment, the WIPI-1 agonist is present in an amount of from about 0.01 wt % to about 10 wt % of the total weight of the composition.

In another embodiment, the current invention encompasses a method for screening active agents useful for improving the aesthetic appearance of skin comprising assaying candidate substances for ability to up-regulate WIPI-1 expression.

In another embodiment, the current invention encompasses a method of treating the skin comprising topically applying to an area of the skin in need thereof an effective amount of an active agent that up-regulates WIPI-1, wherein the ability of said active agent to up-regulate WIPI-1 has been determined by an assay which measures the level of mRNA encoding WIPI-1 in a cell that has been contacted with said active agent.

These and other aspects of the present invention will be better understood by reference to the following detailed description and accompanying figures.

DETAILED DESCRIPTION

Figure 1:
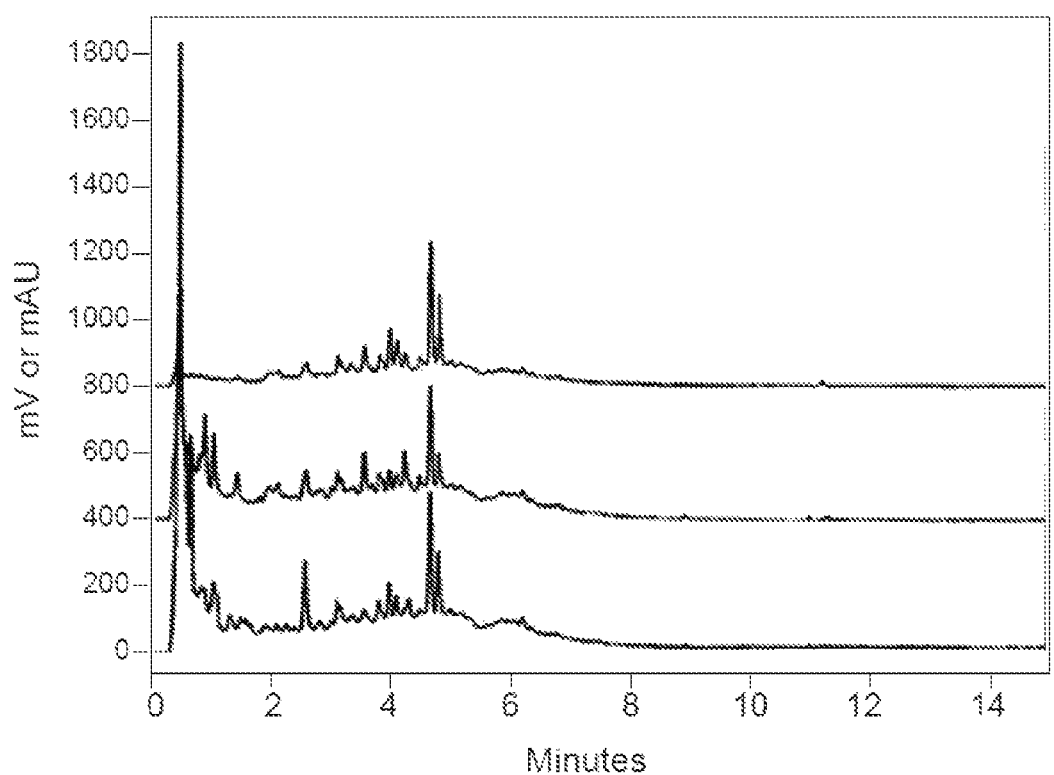
FIG. 1 is a HPLC profile of an extract of *Archidendron clyperia.*

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, and some features may be exaggerated to show details of one embodiment components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

The current invention provides for a new and novel method of treating, preventing, and/or forestalling various manifestations of skin aging or damage through the administration of WIPI-1 agonists to skin in need thereof. In particular, the WIPI-1 agonists seek to treat, prevent, or forestall manifestations of skin aging, such as fine lines, wrinkles, discoloration, etc., by upregulating WIPI-1 and thereby modulating, i.e. increasing, maintaining or restoring, WIPI-1 mediated autophagy activity within the targeted skin cells. The targeted skin cells may include fibroblast, keratinocytes, and/or melanocytes, and in certain embodiments are fibroblasts and/or keratinocytes. The manifestations of skin damage or aging may be due to chronological, hormonal, photo or actinic aging of the skin as well as the constituent skin cells, as well as environmental, nutritional, or heredity issues. Additionally, the WIPI-1 agonists seek to treat, prevent, or forestall manifestations of skin aging or damage, such as fine lines, wrinkles, discoloration, thinning skin, impairment of the skin barrier, by increasing, maintaining, and/or restoring WIPI-1 mediated autophagy activity.

The present invention provides compositions for topical application which comprise an effective amount of a WIPI-1 agonist to treat, reverse, ameliorate and/or prevent signs/manifestations of skin damage or skin aging. Such benefits include without limitation, the following:

(a) treatment, reduction, and/or prevention of fine lines or wrinkles, (b) reduction of skin pore size, (c) improvement in skin thickness, plumpness, and/or tautness;

(d) improvement in skin suppleness and/or softness;

(e) improvement in skin tone, radiance, and/or clarity;

(f) improvement in procollagen and/or collagen production;

(g) improvement in maintenance and remodeling of elastin;

(h) improvement in skin texture and/or promotion of re-texturization;

(i) improvement in skin barrier repair and/or function;

(j) improvement in appearance of skin contours;

(k) restoration of skin luster and/or brightness;

(l) replenishment of essential nutrients and/or constituents in the skin;

(m) improvement of skin appearance decreased by aging and/or menopause;

(n) improvement in skin moisturization and/or hydration;

(o) increase in and/or preventing loss of skin elasticity and/or resiliency;

(p) treatment, reduction, and/or prevention of skin sagging; and/or (q) treatment, reduction, and/or prevention of discoloration of skin.

In practice, the compositions of the invention are applied to skin in need of treatment. That is, skin which suffers from a deficiency or loss in any of the foregoing attributes or which would otherwise benefit from improvement in any of the foregoing skin attributes.

In one embodiment, the composition is intended for use as a non-therapeutic treatment. In another embodiment, the composition is an article intended to be rubbed, poured, sprinkled, or sprayed on, introduced into, or otherwise applied to the human body for cleansing, beautifying, promoting attractiveness, or altering the appearance, in accordance with the US FD&C Act, sec. 201(i).

All terms used herein are intended to have their ordinary meaning unless otherwise provided.

As used herein, the term "consisting essentially of" is intended to limit the invention to the specified materials or steps and those that do not materially affect the basic and novel characteristics of the claimed invention, as understood from a reading of this specification. All percentages are by weight based on the total weight of the composition, unless otherwise indicated.

By "cosmetically acceptable" it is meant that a particular component is generally regarded as safe and nontoxic at the levels employed.

The term "active amount" refers to the amount of WIPI-1 agonist, absent diluent, solvent, carrier, filler or any other ingredient. An "amount effective" or an "effective amount" to provide a particular anti-aging benefit to the skin refers to the "active amount" of WIPI-1 agonist required to provide a clinically measurable improvement in the particular manifestation of skin aging when applied for a time sufficient to provide a clinically measurable improvement in the particular manifestation of aged skin.

The phrase "individual in need thereof" refers to a human who could benefit from improved dermal appearance or health, including males or females.

As used herein, the terms "prevent," "preventing," etc. mean delaying the onset of, hindering the progress of, hindering the appearance of, protection against, inhibiting or eliminating the emergence of, or reducing the incidence of various cosmetic or dermatologic conditions, damages, effects or symptoms. Use of the term "prevention" is not meant to imply that all subjects in a subject population administered the cosmetic composition will always be unaffected by or fail to develop the cosmetic or dermatologic conditions, damage, effect or symptom, but rather that the subject population will exhibit a reduction in the cosmetic or dermatologic damages, effects, or symptoms. For example, many flu vaccines are not 100% effective in preventing the flu in those administered the vaccine.

The term "agonist" encompasses any substance, including, without limitation, organic molecules; chemical compositions; biomolecules (e.g., peptides, proteins, antibodies, nucleic acid oligomers, etc.); and combinations of substances, such as botanical extracts. The agonists up-regulate the cellular levels of WIPI-1, by which is meant that the cellular levels of WIPI-1 are increased by the active agent. The term "up-regulation" may refer to induction, stimulation, potentiation, and/or relief of inhibition. The agonists may be, without limitation, activators, which are compounds that, for example, bind to, stimulate, increase, open, activate, facilitate, enhance activation, sensitize, or up-regulate expression levels of WIPI-1. The mechanism by which the WIPI-1 level is modulated is up-regulated is not important. In some embodiments, WIPI-1 gene expression is increased by at least about 10%, at least about 20%, at least about 30%, at least about 40%, at least about 50%, at least about 60%, at least about 70%, or at least about 80%, compared to the level of WIPI-1 gene expression in the absence of a WIPI-1 agonist. Example 3 below illustrates a method for evaluating the increase in expression of WIPI-1.

As used herein, the term "modulating autophagy activity" refers to an increase, maintenance, restoration, rejuvenation, or enhancement of the level of WIPI-1 mediated autophagy activity within a skin cell. In an embodiment of the current invention, an increase may include about a 10% increase in autophagy activity, about a 20% increase in autophagy activity, about a 30% increase in autophagy activity, about a 40% increase in autophagy activity, about a 50% increase in autophagy activity, and greater than about 50% increase in autophagy activity within the skin cell relative to the autophagy activity prior to the administration of the WIPI-1 agonist. In a further embodiment of the invention, the WIPI-1 agonist may be administered prophylactically to maintain the level of autophagy activity within a skin cell prior to an insult, i.e. exposure to UV radiation for example. In a further embodiment, the autophagy activity within the skin cell may be restored to a level that existed within the skin cell previously, i.e. prior to an insult. In another embodiment the autophagy activity may be rejuvenated and/or enhanced, i.e. increased to the typical level of activity in skin cells younger or of a younger individual than those cells and or individual being treated. Means of determining such levels of activity are detailed in Example 1 below.

As used herein, the term "expression levels" refers to an amount of a gene and/or protein that is expressed in a cell. As used herein, a "gene" includes a polynucleotide containing at least one open reading frame that is capable of encoding a particular polypeptide. As used herein, the terms "polynucleotide" is synonymous with "oligonucleotide" and includes polymeric forms of nucleotides of any length, either deoxyribonucleotides or ribonucleotides, or analogs thereof, including, without limitation, mRNA, DNA, cDNA, primers, probes, and the like.

As used herein, the term "essential oil" refers to the volatile ethereal fraction obtained from a plant or plant part by a physical separation process such as distillation or chromatographic separation. The essential oils are typically terpenoids often comprising monoterpenes and have the odor and flavor of the plant from which they were extracted.

The term "skin" as used herein includes the skin on or in the face, mouth, neck, chest, back, arms, hands, legs, and scalp.

"Treatment" as used herein, as well as related terms such as "treat" or "treating," refers to eradicating, reducing, ameliorating, or reversing one or more of the unwanted features associated with the skin condition being treated, such that the consumer perceives an improvement in the appearance of the skin or other treatment benefit with respect to the condition. Treating aged or aging skin refers to eradicating, reducing, ameliorating, or reversing one or more of the unwanted features associated with aging. Treatment benefits include, e.g., modulating WIPI-1 mediated autophagy activity, reducing fine lines or wrinkles, reducing skin pore size, improving skin thickness, plumpness, and/or tautness; improving skin suppleness and/or softness; improving skin tone, radiance, and/or clarity; improving procollagen and/or collagen production; improving maintenance and remodeling of elastin; improving skin texture and/or promotion of re-texturization; improving in skin barrier repair and/or function; improving appearance of skin contours; restoring skin luster and/or brightness; replenishing essential nutrients and/or constituents in the skin; improving skin appearance decreased by aging and/or menopause; improving skin moisturization and/or hydration; increasing skin elasticity and/or resiliency; reducing skin sagging; and/or reducing discoloration of skin.

In one embodiment, the invention encompasses a screening method for identifying potential WIPI-1 agonists. In one embodiment, an assay is provided for determining the expression levels of WIPI-1 after a cell has been treated, incubated, or otherwise contacted with a candidate substance. The term "candidate substance" refers to any substance that is tested for activity as an agonist of WIPI-1, whether or not the substance is suspected of possessing such activity. The cell can be any cutaneous cell that expresses WIPI-1, and in one embodiment the cells may be fibroblast, keratinocyte, or melanocyte cells, and in a certain embodiment the cells may be fibroblast or keratinocyte cells. In further embodiments, the cell is a human or mouse cell. After the cell has been incubated with a candidate substance for a sufficient length of time to provide a measurable change in expression levels, which will typically be at least one hour, and more typically from about 24 hours to 144 hours (1 to 6 days) it is then lysed to release the cellular components, such as WIPI-1 and mRNA encoding WIPI-1. The amount of WIPI-1 or any subunit thereof may then be measured by any suitable technique for detection and quantitation of peptides and proteins and/or polynucleotides (e.g., mRNA).

In one embodiment, the methods for measuring expression levels of WIPI-1 involve the quantitation of mRNA expression. Suitable methods for determining mRNA expression include quantitative PCR (QPCR), real-time QPCR, reverse transcription PCR (RT-PCR), and quantitative reverse transcription PCR (QRT-PCR), as are well-known in the art. As described in detail in U.S. Pat. Nos. 7,101,663 and 7,662,561, a quantitative reverse transcriptase polymerase chain reaction (QRT-PCR) for detecting mRNA may include the steps of: (a) incubating an RNA sample from the cellular lysate with a reverse transcriptase and a high concentration of a target sequence-specific reverse transcriptase primer under conditions suitable to generate cDNA; (b) subsequently adding suitable polymerase chain reaction (PCR) reagents to the reverse transcriptase reaction, including a high concentration of a PCR primer set specific to the cDNA and a thermostable DNA polymerase to the reverse transcriptase reaction; and (c) cycling the PCR reaction for a desired number of cycles and under suitable conditions to generate PCR products ("amplicons") specific to the cDNA. The products of the QRT-PCR process may be compared after a fixed number of PCR cycles to determine the relative quantity of the RNA species as compared to a given reporter gene, for example, by Southern blotting. More typically, the progress of the PCR reaction is monitored by analyzing the relative rates of amplicon production for each PCR primer set, for example, by (1) non-specific fluorescent dyes that intercalate with any double-stranded DNA, and/or (2) sequence-specific DNA probes consisting of oligonucleotides that are labeled with a fluorescent reporter which permits detection only after hybridization of the probe with its complementary DNA target. The mRNA may be any mRNA known to one of ordinary skill of the art that is associated with WIPI-1.

Additionally, Example 3 below, provides another method for determining the expression levels of WIPI-1 after a cell has been treated, incubated, or otherwise contacted with a candidate substance.

The level of expression in the above disclosed methods of determining WIPI-1 expression levels may be compared to controls that are not treated with the candidate substance to determine the relative degree of modulation. In some embodiments, the candidate substance will up-regulate mRNA expression by at least about 10%, more suitably at least about 20%, at least about 30%, at least about 40%, or at least about 50%. In further embodiments, the candidate substance will up-regulate mRNA expression by at least about 60%, at least about 70%, at least about 80%, at least about 90%, or at least about 100%. Candidate substances meeting these criteria may be selected for use or for further evaluation.

WIPI-1 agonists, identified in accordance with the procedures noted above as shown by Example 4 below, can include naturally occurring or synthetic peptides, amino acids, and chemical entities such as, but not limited to, substituted amino heterocyclic carbamoyl analog as described, for example, in U.S. patent application Ser. No. 13/217,870. In one embodiment, the analog may be:

Analog 1

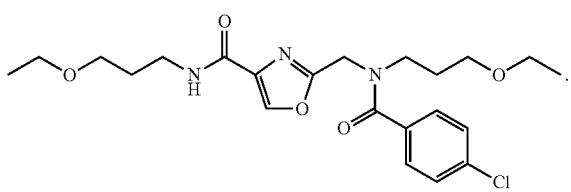

Further, the WIPI-1 agonists may include botanical extracts such as extracts of: *Archidendron clyperia, Ixora chinensis, Maesa japonica, Serrissa japonica, Stephanotis jasminoides, Tiliacora triandra* or any combinations thereof.

*Archidendron clypearia* is an evergreen tree with delicate, dark green foliage with a rounded canopy. It generates small white fuzzy flowers and twisted, bright orange-red fruits. These trees hail from high rainfall areas of north India, through southeastern Asia, such as New Guinea and the Philippines. *Archidendron clypearia* is further described, for example, in U.S. patent application Ser. No. 13/216,626, filed on Aug. 24, 2011, herein incorporated by reference in its entirety for all purposes.

*Ixora chinensis* is a flowering plant native to southern China that is characterized by its almost stalkless leaves and red flowers. It is used to treat various ailments like rheumatism and wounds, and is described, for example, in U.S. patent application Ser. No. 13/158,947 filed on Jun. 30, 2010, and U.S. patent application Ser. No. 13/324,150, filed on Dec. 13, 2011, herein incorporated by reference in its entirety for all purposes.

*Maesa japonica* is a small to medium sized evergreen shrub with sometimes scandent stems, bearing alternate *Aucuba*-like ovate-broadly elliptic dentate leaves of a much thinner texture. Bearing in all the axils short congested racemes of creamy-white flowers, that bear the palest pink fleshy berries. *Maesa japonica* is further described in U.S. application Ser. No. 13/710,585, entitled "*Maesa japonica* extracts and methods of use" filed on Dec. 11, 2012 to Siming Chen et. al, herein incorporated by reference in its entirety for all purposes.

*Serissa japonica*, also known as the tree of a thousand stars, is an evergreen shrub with small, bright green, oval leaves that is native to open sub-tropical woodlands and wet meadows in southeast Asia. Depending on the variety, small white or pink flowers cover the tree in late spring. The natural color of the trunk is gray and the bark roughens with age. *Serissa japonica* is further described in PCT Application Serial No. PCT/US12/68858, entitled "*Serissa japonica* extracts and methods of use", to Qian Zheng et al. and filed on Dec. 11, 2012, the entirety of which is incorporated herein in its entirety for all purposes.

*Stephanotis jasminoides*, also known as Madagascar Jasmine, is a twining and branched evergreen climber with shiny, thick, dark green, oval leaves. The evergreen produces fragrant, waxy white flowers bloom from spring to fall. *Stephanotis jasminoides* is further described in PCT Application Serial No. PCT/US12/68866, entitled "*Stephanotis jasminoides* extracts and methods of use", to Permanan Raaj Khusial et al. and filed on Dec. 11, 2012, the entirety of which is incorporated herein in its entirety for all purposes.

*Tiliacora triandra* ("Yanang") is a species of flowering plant native to mainland Southeast Asia and used particularly in the cuisines of northeast Thailand and Laos. In traditional Southeast Asian medicine, *Tiliacora triandra* has been used as an herbal medicine for fever relief, alcohol intoxication, inflammation, and bacterial/fungal infection. For instance, the use of *Tiliacora triandra* Diels against *plasmodium falciparum* (cause malaria in humans) is disclosed in Pavanand et al., Phytother. Res., 3, 215-217 (1989), and is described, for example, in U.S. patent application Ser. No. 12/345,707 (U.S. Pub. 2010.0166677), filed on Dec. 30, 2008; Ser. No. 13/158,947 (U.S. Pub. No. 2012.0003332), filed on Jun. 30, 2010; and Ser. No. 12/827,001 (U.S. Pub. No. 2012/0003331), filed on Jun. 30, 2010, the entirety of which is incorporated herein in its entirety for all purposes.

The above-noted extracts contain a number of active compounds, one or more of which upregulate WIPI-1. In certain embodiments of the current invention, WIPI-1 agonists may exclude one or more of the above-noted compounds and/or extracts, and in another embodiment extracts of *Tiliacora triandra* may be excluded.

The plant materials may be in any form including, but not limited to, the whole plant, a dried plant, a ground plant, or parts thereof, including but not limited to, seeds, needles, leaves, roots, bark, cones, stems, rhizomes, callus cells, protoplasts, flowers, and meristems, or components and/or constituents found in, or isolated from, the natural plant material, and/or portions of the plant, or any combinations thereof. In one embodiment, the natural plant material is in the form of an extract derived from the whole plant or from a select portion of the plant, such as the leaves of the plant. In certain embodiments directed to *Archidendron clyperia, Serissa japonica*, or [[*Maesa japonica*]] the extract may be derived from the stems and leaves of the plants. In embodiments where *Ixora chininensis* is used the extract may be derived from its flowers, and in the case of *Tiliacora triandra* the extract may be derived from vines of the plant. It is to be understood that "natural plant material" also includes an ingredient, component, constituent, or extract derived from the natural plant material.

Specifically, the botanical component is derived from raw materials collected from the plants, which may contain the desired constituent(s), such as seeds, needles, leaves, roots, bark, cones, stems, rhizomes, callus cells, protoplasts, organs and organ systems, and meristems. In certain embodiments, the raw materials collected from the plants are ground to small particle sizes. In addition, the raw materials may be dried to reduce water content. The raw materials may be dried by a number of different means, such as, for example, air-dried, oven-dried, rotary evaporated under vacuum or lyophilized.

The extract of the above-noted plants may be obtained by distilling the raw materials with a stripping agent. The stripping agent may be a liquid that is miscible, immiscible, or partially miscible with the desired extract from the plants. Suitable stripping agents include, but are not limited to, water; alcohols (such as methanol, ethanol, propanol, butanol and the like); glycols; ethers (such as diethyl ether, dipropyl ether, and the like); esters (such as butyl acetate, ethyl acetate, and the like); ketones (such as acetone, ethyl methyl ketone, and the like); dimethyl sulfoxide; acetonitrile; other organic solvents; and combinations thereof. In one embodiment, the stripping agent is immiscible with the desired extract (e.g., essential oil) from the plant. In a further embodiment, the stripping agent is water. The extract is obtained by steam distillation in yet another embodiment. The extract (e.g., essential oil) may be collected by phase separation from the stripping agent. It is believed that the stripping agent increases the overall vapor pressure of a distillation system for obtaining an extract and thereby reducing the boiling point of the desired product, the extract.

In other embodiments, the botanical component may be in the form of an extract obtained by solvent extraction, in one embodiment the extract may be obtained by an organic solvent extraction. Briefly, the organic solvent extraction method involves washing and extracting the raw materials, which may be whole or ground into small particle sizes, using an organic solvent. Non-limiting examples of organic solvents include methanol, ethanol, isopropanol, dichloromethane, chloroform, hexane, xylene, and petroleum ether. An extracting machine may be used for organic solvent extraction as is well known in the field. The raw materials are pushed in the extracting machine by a thruster, which slowly moves the plant raw materials forward. Organic solvent (e.g., ethanol) may be added into the machine through a solvent inlet at the top of a waste discharge outlet. Due to the difference in gravity and equilibrium, the solvent flows toward the raw material inlet, soaks the materials and flows out from the opposite side of the solvent inlet. Since the plant materials and the solvent move in opposite directions against each other, the plant materials are constantly immersed in a solution that contains a low-concentration of extract. As a result of equilibrium, high yield of plant constituent(s) may be achieved by continuously extracting the plant material against the low-concentration solution.

An extraction time suitable to extract the plant constituents is used, typically between about 1-10 hours is suitable, and in another embodiment between about 2-8 hours is suitable, and in a further embodiment between about 3-6 hours is suitable. The temperature of extraction is between about 30° C.-100° C., in a further embodiment is between about 40° C.-70° C., and in yet another embodiment is between about 50° C.-60° C. The collected extract is then fine-filtered to remove debris, and may be used directly, or is concentrated, for example by distilling the solvent or by other conventional processing. The solution of extract actives may be rotary evaporated under vacuum or lyophilized. A typical extract's actives content is above about 25%, in a further embodiment above 50%, and the extract can also be provided as an essential oil or a concentrate having a semi-solid or solid consistency.

Similarly, aqueous-organic solvent extraction involves initially collecting raw materials from the above-noted plants, which may be whole or ground into small particle sizes. The ground plant material is soaked in aqueous solution that is acidic or alkaline, depending on the solubility and stability of the desired extract under acidic or alkaline (basic) conditions. For extraction under acidic conditions, an acid such as hydrochloric acid or sulfuric acid is added to water, e.g., at a concentration of about 3% (w/v). For extraction under alkaline conditions, an alkali such as sodium hydroxide or sodium carbonate is added to water. The extraction time and temperature of extraction are typically similar to that used in the organic solvent extraction method described above.

The extract is then collected and fine-filtered to remove debris. Alkaline agents (e.g., ammonia) or acidifying agents (e.g., sulfuric acid) may be added to the extract to neutralize the solution by adjusting the pH, depending on the acidity or alkalinity of the collected extract. The aqueous extract may be used directly, concentrated or dried. Alternatively, organic solvent may then be added to the neutralized solution to transfer the extract from an aqueous phase to an organic phase. Examples of such organic solvents include, but are not limited to, ethanol, isopropanol, butanol, pentanol, hexanol and xylene. The extract comprising the transferred extract actives dissolved in organic solvent may be used directly as an essential oil or a concentrate, or dried by a number of different means, such as, for example, air-dried, oven-dried, rotary evaporated under vacuum or lyophilized to a semi-solid or solid consistency.

It should also be noted that different plants containing different constituents can be mixed and extracted together. This process of mixed extraction can in one embodiment be used for extracting those plants containing constituents with similar solubility in the solvent used for extraction, such as ethanol. The mixture of extracts can be concentrated and stored in an appropriate solvent.

In another embodiment, extract as used herein, also includes "synthetic" extracts, i.e., various combinations of known plant components and/or constituents that are combined to substantially mimic the composition and/or activity of any one or more of the above-noted plant extracts of natural origin having adipose septa protein modulating activities. In one embodiment, the synthetic extracts have substantially the same number of active components as the natural plant material. The correspondence of the numerical incidence of actives between the synthetic extracts and the natural plant material may also be described in terms of "percent commonality." The synthetic extract has about 50 percent or more commonality to the chemical composition of a plant or natural extract. In other words, the synthetic extract has about 50 percent or more of the active ingredients found in the plant or a natural extract. In further embodiments, the chemical composition of the synthetic extract has about 70 percent or more commonality to the chemical composition of a plant or a natural extract. Optimally, a synthetic extract has about 90 percent or more commonality to the chemical composition of a plant or a natural extract.

In a further embodiment of the current invention, extracts/metabolites may be obtained from plant tissue cultures. In one embodiment, extracts/metabolites of *Stephanotis jasminoides* may be obtained from a plant cell culture. In general, the highly controlled environment of a bioreactor may be used in one embodiment to produce repeatable and/or reliable extracts. The ability to control the environment in a bioreactor also facilitates the use of various elicitors to stimulate or control the production and ratios of beneficial chemicals (and optionally to reduce undesired chemicals).

Methods of culturing plant cell tissues used herein are conventional, see U.S. Patent Application No. 20110159121. By way of example, the following are recognized textbooks that provide teachings in this area: *Plant Cell and Tissue Culture, a Laboratory Manual*, Reinert & Yoeman, Springer-Verlag 1982 (ISBN 3-540-11316-9); *Plant Tissue Culture Propagation*, de Fossard, Filmfiche Corp. 1981 (ISBN 0-949801-003); *In Vitro Culture of Higher Plants*, Pierik, Martinus Nijhoff Publishers 1987 (ISBN 90-247-3531-9); *Plant Culture Media, Volume 1, Formulations and Uses*, George, Puttock & George, Exegetics Ltd. 1987 (ISBN 0-9509325-2-3); *Plant Cell Culture Secondary Metabolism: toward industrial application*, DiCsomo & Misawa, CRC Press LLC 1996 (ISBN 0-8493-5135-9); *Plant Tissue Culture: Theory and Practice, a revised edition*, Bhojwani & Rasdan, Elsevier 1996 (ISBN 0-444-81623-2); *Plant Cell Culture Protocols*, $2^{nd}$ Ed., Loyola-Vargas & Vazquez-Floga, Humana Press 2006 (ISBN 1-59259-959-1); and so forth.

A plant tissue culture may be generated from any part of the plant, including for instance topical meristem or bud, root (including root tip, root hairs, and so forth), stem/trunk (including bark peels, exocarp, endocarp, phloem, xylem, and so forth), leaf (including leaf parts and injured portions thereof), flower (including parts of flowers, such as anther, petals, stamen, pistil, etc.), pollen, seed (and parts of seeds), fruit (and parts or portions of fruits, such as peel, pulp, seed, etc.), cuticle, and so forth. In one embodiment, the tissue culture is derived from the meristem or injured leaf tissue. The tissue/cells may then be cultivated on a conventional plant cell culture medium which is well known to the person skilled in the art. Examples of such plant cell culture media conventionally used by the person skilled in the art are described in the following works: E. F. Georges, D. J. Puttock and J. G. Heather, (1987) Plant Culture Media, (Volume 1, Formulations and uses), Exegetics Ltd; Dodds J. H. Roberts L. W. (1982). Experiments in Plant Tissue Culture. Cambridge Univ. Press, Cambridge. 178 pp.; Evans D. A., Sharp W. R., Ammirato P. V., Yamada Y. (1984). Handbook of Plant Cell Culture. Techniques for Propagation and Breeding. Macmillan Publ. Co., New York, 970 pp., Vols. 1 to 6; Reinert J., Yeoman M. M. (1982). Plant Cell and Tissue Culture. A Laboratory Manual. Springer-Verlag, Berlin, Heidelberg, N.Y. 83 pp.; Sala F., Parisi B., Cella R., Cifferi O. (1980). Plant cell cultures. Elsevier/North Holland, Amsterdam; Sharp W. R., Larsen P. O., Paddock E. F., Raghavan V. (1979); Plant Cell and tissue culture. Principles and applications. Ohio State University Press, Columbus; Vasil I. (1985-1991). Cell Culture and Somatic Cell Genetics of Plants. Vols. 1 to 8; Bhojwani S., Razdan I. Z. K. (1983). Plant tissue culture: theory and practice. Elsevier, Amsterdam; Debergh P., Zimmermann (1991). Micropropagation. Technology and application. Kluwer, London; and Zyrd J. P. (1988). Cultures de cellules, tissus et organes végétaux [Plant organ, tissue and cell cultures]. Presses Polytechniques Romandes, Lausanne. The resulting cultures are selected for desired traits and subcultured over a number of weeks to provide an aggregate of undifferentiated cells, referred to as calli, possessing the desired traits.

The calli possessing the desired traits may then be transferred to liquid medium in a bio reactor where they are held in suspension. The liquid medium and the conditions of the bioreactor are optimized for the calli's growth. Suitable nutrient media for plant cell suspension culture are well known to one of skill in the art. In a particular example, a plant cell suspension culture medium includes Murashige and Skoog (MS) salts (e.g., Cat. No. M524, Phytotech, Shawnee Mission, Kans.) and Nitsch and Nitsch vitamins (e.g., Cat. No. N608, Phytotech, Shawnee Mission, Kans.). See, e.g., Nitsch and Nitsch, Science 163:85-87, 1969.

Optionally, cells in culture may be subjected to an elicitation step prior to extraction or harvesting of metabolite(s) from the culture. Elicitors of various types may be used to expose or treat the plant tissue thus eliciting a response from the tissue in the gene expression and production of chemicals that are desirable or beneficial or to alter the ratio of chemicals. Cell elicitation can be effected by means of agents or by means of various stresses, such as pressure, depressurization, vacuum, pressure variations, the presence of a gas, a variable atmosphere, temperature, cold, light intensity or spectral distribution or ratio or cycle of brightness, radiation, a toxin, a plant toxin, a plant extract other than a toxin, an antioxidant or blend thereof, agitation, a bacterium, a virus, fungi, a microorganism, ultrasound, IR, UV, asphyxia, etc. Any method of elicitation known to one skilled in the art can be used to stimulate tissue cultures as described herein. It is further contemplated that other organic or inorganic chemicals/substances (including elements) may be useful to influence expression (and/or metabolite production) in the cell culture. For example production of a specific antioxidant compound(s) may be initiated or the production increased after exposure to a plant pathogen, or an environmental challenge such as simulated drought or cold or a chemical present in insect saliva simulating an insect attack.

Subsequently, tissue plant culture may be homogenized and followed by extraction stages and by various filtrations followed by freeze-drying in order to incorporate the extracts obtained in a cosmetic or pharmaceutical preparation. Such methods are described, for example, in U.S. Pat. No. 4,241,536; U.S. published application 2005/0265953, EP 378 921, WO 88/00968, EP 1 203 811, and so forth.

In one embodiment, cells are propagated in a plant tissue culture using methods know to those of ordinary skill of the art to quickly generate a "clean stock" from which the active ingredients may be isolated.

The cosmetic compositions according to the invention can be formulated in a variety of forms for topical application and will comprise from about 0.00001% to about 90% by weight of one or more actives that upregulate WIPI-1, and in other embodiments will comprise such actives in an amount from about 0.001% to about 25% by weight, and in a further embodiment it will comprise such actives in an amount from about 0.001% to about 1% by weight.

Another embodiment of the invention encompasses compositions comprising a cosmetically or dermatologically acceptable formulation which is suitable for contact with living animal tissue, including human tissue, with virtually no adverse physiological effect to the user. Compositions embraced by this invention can be provided in any cosmetically and/or dermatologically suitable form, in one embodiment as a lotion or cream, but also in an anhydrous or aqueous base, as well as in a sprayable liquid form. Other suitable cosmetic product forms for the compositions of this invention include, for example, an emulsion, a cream, a balm, a gloss, a lotion, a mask, a serum, a toner, an ointment, a mousse, a patch, a pomade, a solution, a spray, a wax-based stick, or a towelette. In addition, the compositions contemplated by this invention can include one or more compatible cosmetically acceptable adjuvants commonly used and known by the skilled practitioner, such as colorants, fragrances, emollients, humectants, preservatives, vitamins, chelators, thickeners, perilla oil or perilla seed oil (WO 01/66067 to a "Method of Treating a Skin Condition,") and the like, as well as other botanicals such as aloe, chamomile, and the like, and as further described below.

Also, embraced by the invention are transdermal modes of delivery, such as patches and the like, with or without suitable penetration enhancers. The methods and compositions embodied by the invention provide a means by which the WIPI-1 agonists can be effectively administered in a transdermal system. Accordingly, a transdermal means of delivering a composition or formulation (often with a penetration enhancing composition) to the skin is that of the transdermal patch or a similar device as known and described in the art. Transdermal patches are designed to deliver an effective amount of compound across a user's skin. Transdermal patches typically involve a liquid, gel, solid matrix, or pressure-sensitive adhesive carrier into which one or more of the above noted extracts may be incorporated. Patch formulations and preparations are well known in the art. See for example "Dermatological and Transdermal Formulations" (Drugs and the Pharmaceutical Sciences, Vol 119) by Kenneth A Walters (Editor), Marcel Dekker and "Transdermal Drug Delivery" (Drugs & the Pharmaceutical Sciences) by Richard H. Guy (Editor), Jonathan Hadgraft (Editor) 2nd Rev& ex edition Marcel Dekker and "Mechanisms of Transdermal Drug Delivery" (Drugs & the Pharmaceutical Sciences, Vol 83) edited by Russell O. Potts and Richard H. Guy (1997). Examples of such devices are disclosed in U.S. Pat. Nos. 5,146,846; 5,223,262; 4,820,724; 4,379,454; and 4,956,171; and U.S. Patent Publication No. US20110300198. The transdermal mode of storing and delivering the compositions onto the skin, including hair, and forming the active composition is convenient and well-suited for the purposes of an embodiment of the present invention. In another method, the application is through a sustained release vehicle, carrier, or diluent, e.g., a topically applied sustained released patch. When a topical patch is used, the patch may be applied to the desired area for extended period of time. The extended period of time may be greater than one hour, and in certain embodiments the extended period of time is overnight, i.e., when the user is sleeping. In a further embodiment of the current invention, the transdermal patch may be applied to aged skin or skin at risk for aging, i.e., uv exposed skin, for extended periods of time, at least one day, two or more days, at least a week, or longer if necessary in order to provide prolonged exposure to the WIPI-1 agonists in order to achieve the desired enhancements to the aged or aging skin.

The compositions can include a cosmetically acceptable vehicle. Such vehicles may take the form of any known in the art suitable for application to skin and may include water (e.g., deionized water); vegetable oils; mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicone, dimethicone, dimethicone cross-polymer, polysiloxanes and their derivatives, such as organomodified derivatives; hydrocarbon oils such as mineral oil, petrolatum, isoeicosane and polyisobutene; polyols such as propylene glycol, glycerin, butylene glycol, pentylene glycol and hexylene glycol; waxes such as beeswax and botanical waxes; or any combinations or mixtures of the foregoing.

The vehicle may comprise an aqueous phase, an oil phase, an alcohol, a silicone phase or mixtures thereof. The cosmetically acceptable vehicle may also comprise an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions. The emulsion may include an emulsifier, such as a nonionic, anionic or amphoteric surfactant.

The oil phase of the emulsion in one embodiment has one or more organic compounds, including emollients; humectants (such as butylene glycol, propylene glycol, Methyl gluceth-20, and glycerin); other water-dispersible or water-soluble components including thickeners such as veegum or hydroxyalkyl cellulose; gelling agents, such as high MW polyacrylic acid, i.e. CARBOPOL 934; and mixtures thereof. The emulsion may have one or more emulsifiers capable of emulsifying the various components present in the composition.

The compounds suitable for use in the oil phase include without limitation, vegetable oils; esters such as octyl palmitate, isopropyl myristate and isopropyl palmitate; ethers such as dicapryl ether; fatty alcohols such as cetyl alcohol, stearyl alcohol and behenyl alcohol; isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; natural or synthetic waxes; and the like. Suitable hydrophobic hydrocarbon oils may be saturated or unsaturated, have an aliphatic character and be straight or branched chained or contain alicyclic or aromatic rings. The oil-containing phase may be composed of a singular oil or mixtures of different oils.

Hydrocarbon oils including those having 6-20 carbon atoms may be utilized, and in one embodiment they may have 10-16 carbon atoms. Representative hydrocarbons include decane, dodecane, tetradecane, tridecane, and $C_{8-20}$ isoparaffins. Paraffinic hydrocarbons are available from Exxon under the ISOPARS trademark, and from the Permethyl Corporation. In addition, $C_{8-20}$ paraffinic hydrocarbons such as $C_{12}$ isoparaffin (isododecane) manufactured by the Permethyl Corporation having the tradename Permethyl 99 A™ are also contemplated to be suitable. Various commercially available $C_{16}$ isoparaffins, such as isohexadecane (having the tradename Permethyl®) are also suitable. Examples of volatile hydrocarbons include polydecanes such as isododecane and isodecane, including for example, Permethyl-99A (Presperse Inc.) and the $C_7$-$C_8$ through $C_{12}$-$C_{15}$ isoparaffins such as the Isopar Series available from Exxon Chemicals. A representative hydrocarbon solvent is isododecane.

The oil phase may comprise one or more waxes, including for example, rice bran wax, carnauba wax, ouricurry wax, candelilla wax, montan waxes, sugar cane waxes, ozokerite, polyethylene waxes, Fischer-Tropsch waxes, beeswax, microcrystalline wax, silicone waxes, fluorinated waxes, and any combination thereof.

Non-limiting emulsifiers include emulsifying waxes, emulsifying polyhydric alcohols, polyether polyols, polyethers, mono- or di-ester of polyols, ethylene glycol mono-stearates, glycerin mono-stearates, glycerin di-stearates, silicone-containing emulsifiers, soya sterols, fatty alcohols such as cetyl alcohol, acrylates, fatty acids such as stearic acid, fatty acid salts, and mixtures thereof. Emulsifiers may include soya sterol, cetyl alcohol, stearic acid, emulsifying wax, acrylates, silicone containing emulsifiers and mixtures thereof. Other specific emulsifiers that can be used in the composition of the present invention include, but are not limited to, one or more of the following: $C_{10-30}$ alkyl acrylate crosspolymer; Dimethicone PEG-7 isostearate, acrylamide copolymer; mineral oil; sorbitan esters; polyglyceryl-3-diisostearate; sorbitan monostearate, sorbitan tristearate, sorbitan sesquioleate, sorbitan monooleate; glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; dimethicone copolyols; polyglyceryl esters such as polyglyceryl-3-diisostearate; glyceryl laurate; Steareth-2, Steareth-10, and Steareth-20, to name a few. Additional emulsifiers are provided in the INCI Ingredient Dictionary and Handbook $11^{th}$ Edition 2006, the disclosure of which is hereby incorporated by reference in its entirety.

These emulsifiers typically will be present in the composition in an amount from about 0.001% to about 10% by weight, in particular in an amount from about 0.01% to about 5% by weight, and in one embodiment, from about 0.1% to about 3% by weight.

The oil phase may comprise one or more volatile and/or non-volatile silicone oils. Volatile silicones include cyclic and linear volatile dimethylsiloxane silicones. In one embodiment, the volatile silicones may include cyclodimethicones, including tetramer ($D_4$), pentamer ($D_5$), and hexamer ($D_6$) cyclomethicones, or mixtures thereof. Particular mention may be made of the volatile cyclomethicone-hexamethyl cyclotrisiloxane, octamethyl-cyclotetrasiloxane, and decamethyl-cyclopentasiloxane. Suitable dimethicones are available from Dow Corning under the name Dow Corning 200® Fluid and have viscosities ranging from 0.65 to 600,000 centistokes or higher. Suitable non-polar, volatile liquid silicone oils are disclosed in U.S. Pat. No. 4,781,917. Additional volatile silicones materials are described in Todd et al., "Volatile Silicone Fluids for Cosmetics", Cosmetics and Toiletries, 91:27-32 (1976). Linear volatile silicones generally have a viscosity of less than about 5 centistokes at 25° C., whereas the cyclic silicones have viscosities of less than about 10 centistokes at 25° C. Examples of volatile silicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G.E. Silicones), GE 7207 and 7158 (General Electric Co.); and SWS-03314 (SWS Silicones Corp.). Linear, volatile silicones include low molecular weight polydimethylsiloxane compounds such as hexamethyldisiloxane, octamethyltrisiloxane, decamethyltetrasiloxane, and dodecamethylpentasiloxane, to name a few.

Non-volatile silicone oils will typically comprise polyalkylsiloxanes, polyarylsiloxanes, polyalkylarylsiloxanes, or mixtures thereof. Polydimethylsiloxanes are non-volatile silicone oils. The non-volatile silicone oils will typically have a viscosity from about 10 to about 60,000 centistokes at 25° C., in one embodiment between about 10 and about 10,000 centistokes, and in one embodiment still between about 10 and about 500 centistokes; and a boiling point greater than 250° C. at atmospheric pressure. Non limiting examples include dimethyl polysiloxane (dimethicone), phenyl trimethicone, and diphenyldimethicone. The volatile and non-volatile silicone oils may optionally be substituted with various functional groups such as alkyl, aryl, amine groups, vinyl, hydroxyl, haloalkyl groups, alkylaryl groups, and acrylate groups, to name a few.

The water-in-silicone emulsion may be emulsified with a nonionic surfactant (emulsifier) such as, for example, polydiorganosiloxane-polyoxyalkylene block copolymers, including those described in U.S. Pat. No. 4,122,029. These emulsifiers generally comprise a polydiorganosiloxane backbone, typically polydimethylsiloxane, having side chains comprising -(EO)$_m$— and/or —(PO)$_n$— groups, where EO is ethyleneoxy and PO is 1,2-propyleneoxy, the side chains being typically capped or terminated with hydrogen or lower alkyl groups (e.g., $C_{1-6}$, typically $C_{1-3}$). Other suitable water-in-silicone emulsifiers are disclosed in U.S. Pat. No. 6,685,952. Commercially available water-in-silicone emulsifiers include those available from Dow Corning under the trade designations 3225C and 5225C FORMULATION AID; SILICONE SF-1528 available from General Electric; ABIL EM 90 and EM 97, available from Goldschmidt Chemical Corporation (Hopewell, Va.); and the SILWET series of emulsifiers sold by OSI Specialties (Danbury, Conn.).

Examples of water-in-silicone emulsifiers include, but are not limited to, dimethicone PEG 10/15 crosspolymer, dimethicone copolyol, cetyl dimethicone copolyol, PEG-15 lauryl dimethicone crosspolymer, laurylmethicone crosspolymer, cyclomethicone and dimethicone copolyol, dimethicone copolyol (and) caprylic/capric triglycerides, polyglyceryl-4 isostearate (and) cetyl dimethicone copolyol (and) hexyl laurate, and dimethicone copolyol (and) cyclopentasiloxane. In one embodiment examples of water-in-silicone emulsifiers include, without limitation, PEG/PPG-18/18 dimethicone (trade name 5225C, Dow Corning), PEG/PPG-19/19 dimethicone (trade name BY25-337, Dow Corning), Cetyl PEG/PPG-10/1 dimethicone (trade name Abil EM-90, Goldschmidt Chemical Corporation), PEG-12 dimethicone (trade name SF 1288, General Electric), lauryl PEG/PPG-18/18 methicone (trade name 5200 FORMULATION AID, Dow Corning), PEG-12 dimethicone crosspolymer (trade name 9010 and 9011 silicone elastomer blend, Dow Corning), PEG-10 dimethicone crosspolymer (trade name KSG-20, Shin-Etsu), dimethicone PEG-10/15 crosspolymer (trade name KSG-210, Shin-Etsu), and dimethicone PEG-7 isostearate.

The water-in-silicone emulsifiers typically will be present in the composition in an amount from about 0.001% to about 10% by weight, in another embodiment in an amount from about 0.01% to about 5% by weight, and in a further embodiment in an amount below 1% by weight.

The aqueous phase of the emulsion may include one or more additional solvents, including lower alcohols, such as ethanol, isopropanol, and the like. The volatile solvent may also be a cosmetically acceptable ester such as butyl acetate or ethyl acetate; ketones such as acetone or ethyl methyl ketone; or the like.

The oil-containing phase will typically comprise from about 10% to about 99%, about 20% to about 85%, or from about 30% to about 70% by weight, based on the total weight of the emulsion, and the aqueous phase will typically comprise from about 1% to about 90%, about 5% to about 70%, or from about 20% to about 60% by weight of the total emulsion.

The compositions may include liposomes. The liposomes may comprise other additives or substances and/or may be modified to more specifically reach or remain at a site following administration.

The composition may optionally comprise other cosmetic actives and excipients, obvious to those skilled in the art including, but not limited to, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants, fragrances, colorants, depigmenting agents, hypopigmenting agents, preservatives (e.g., DMDM Hydantoin/Iodopropynylbutylcarbonate), stabilizers, pharmaceutical agents, photostabilizing agents, neutralizers (e.g., triethanolamine) and mixtures thereof. In addition to the foregoing, the cosmetic compositions of the invention may contain any other compound for the treatment of skin disorders.

Colorants may include, for example, organic and inorganic pigments and pearlescent agents. Suitable inorganic pigments include, but are not limited to, titanium oxide, zirconium oxide and cerium oxide, as well as zinc oxide, iron oxide, chromium oxide and ferric blue. Suitable organic pigments include barium, strontium, calcium, and aluminium lakes and carbon black. Suitable pearlescent agents include mica coated with titanium oxide, with iron oxide, or with natural pigment.

Various fillers and additional components may be added. Fillers are normally present in an amount of about 0 weight % to about 20 weight %, based on the total weight of the composition, in one embodiment about 0.1 weight % to about 10 weight %. Suitable fillers include without limitation silica, treated silica, talc, zinc stearate, mica, kaolin, Nylon powders such as Orgasol™, polyethylene powder, Teflon™, starch, boron nitride, copolymer microspheres such as Expancel™ (Nobel Industries), Polytrap™ (Dow Corning) and silicone resin microbeads (Tospearl™ from Toshiba), and the like.

In one embodiment of the invention, the compositions may include additional skin actives such as, but not limited to, botanicals, keratolytic agents, desquamating agents, keratinocyte proliferation enhancers, collagenase inhibitors, elastase inhibitors, depigmenting agents, anti-inflammatory agents, steroids, anti-acne agents, antioxidants, salicylic acid or salicylates, thiodipropionic acid or esters thereof, and advanced glycation end-product (AGE) inhibitors.

In a specific embodiment, the composition may comprise at least one additional botanical, such as, for example, a botanical extract, an essential oil, or the plant itself. Suitable botanicals include, without limitation, extracts from *Abies pindrow, Acacia catechu, Anogeissus latifolia, Asmunda japonica, Azadirachta indica, Butea frondosa, Butea monosperma, Cedrus deodara, Emblica officinalis, Ficus benghalensis, Glycyrrhiza glabra, Ilex purpurea Hassk, Inula racemosa, Ligusticum chuangxiong, Ligusticum lucidum, Mallotus philippinensis, Mimusops elengi, Morinda citrifolia, Moringa oleifera, Naringi crenulata, Nerium indicum, Psoralea corylifolia, Stenoloma chusana, Terminalia bellerica*, tomato glycolipid and mixtures thereof.

The composition may comprise additional active ingredients having anti-aging benefits, as it is contemplated that synergistic improvements may be obtained with such combinations. Exemplary anti-aging components include, without limitation, botanicals (e.g., *Butea frondosa* extract); thiodipropionic acid (TDPA) and esters thereof; retinoids (e.g., all-trans retinoic acid, 9-cis retinoic acid, phytanic acid and others); hydroxy acids (including alpha-hydroxyacids and beta-hydroxyacids), salicylic acid and salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); barrier function enhancing agents (e.g., ceramides, glycerides, cholesterol and its esters, alpha-hydroxy and omega-hydroxy fatty acids and esters thereof, etc.); collagenase inhibitors; and elastase inhibitors; to name a few.

Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

In another embodiment, the topical compositions of the present invention may also include one or more of the following: a skin penetration enhancer, an emollient, a skin plumper, an optical diffuser, a sunscreen, an exfoliating agent, and an antioxidant.

An emollient provides the functional benefits of enhancing skin smoothness and reducing the appearance of fine lines and coarse wrinkles. Examples include isopropyl myristate, petrolatum, isopropyl lanolate, silicones (e.g., methicone, dimethicone), oils, mineral oils, fatty acid esters, cetyl ethylhexanoate, C12-15 alkyl benzoate, isopropyl isostearate, diisopropyl dimer dillinoeate, or any mixtures thereof. The emollient may be present from about 0.1 wt % to about 50 wt % of the total weight of the composition.

A skin plumper serves as a collagen enhancer to the skin. An example of a suitable skin plumper is palmitoyl oligopeptide. Other skin plumpers are collagen and/or other glycosaminoglycan (GAG) enhancing agents. When present, the skin plumper may comprise from about 0.1 wt % to about 20 wt % of the total weight of the composition.

An optical diffuser is a particle that changes the surface optometrics of skin, resulting in a visual blurring and softening of, for example, lines and wrinkles. Examples of optical diffusers that can be used in the present invention include, but are not limited to, boron nitride, mica, nylon, polymethylmethacrylate (PMMA), polyurethane powder, sericite, silica, silicone powder, talc, Teflon, titanium dioxide, zinc oxide, or any mixtures thereof. When present, the optical diffuser may be present from about 0.01 wt % to about 20 wt % of the total weight of the composition.

A sunscreen for protecting the skin from damaging ultraviolet rays may also be included. In one embodiment sunscreens may include those with a broad range of UVB and UVA protection, such as octocrylene, avobenzone (Parsol 1789), octyl methoxycinnamate, octyl salicylate, oxybenzone, homosylate, benzophenone, camphor derivatives, zinc oxide, and titanium dioxide. When present, the sunscreen may comprise from about 0.01 wt % to about 70 wt % of the composition.

Suitable exfoliating agents include, for example, alpha-hydroxyacids, beta-hydroxyacids, oxaacids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. In one embodiment exfoliating agent is glycolic acid. When present, the exfoliating agent may comprise from about 0.1 wt % to about 80 wt % of the composition.

Antioxidants scavenge free radicals from skin, protecting the skin from environmental aggressors. Examples of antioxidants that may be used in the present compositions include compounds having phenolic hydroxy functions, such as ascorbic acid and its derivatives/esters; alpha-hydroxyacids; beta-carotene; catechins; curcumin; ferulic acid derivatives (e.g. ethyl ferulate, sodium ferulate); gallic acid derivatives (e.g., propyl gallate); lycopene; reductic acid; rosmarinic acid; tannic acid; tetrahydrocurcumin; tocopherol and its derivatives (e.g., tocopheryl acetate); uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may comprise an antioxidant in one embodiment from about 0.001 wt % to about 10 wt %, and in one embodiment from about 0.01 wt % to about 5 wt %, of the total weight of the composition.

Other conventional additives include: vitamins, such as tocopherol and ascorbic acid; vitamin derivatives such as ascorbyl monopalmitate; thickeners such as hydroxyalkyl cellulose; gelling agents; structuring agents such as bentonite, smectite, magnesium aluminum silicate and lithium magnesium silicate; metal chelating agents such as EDTA; pigments such as zinc oxide and titanium dioxide; colorants; emollients; and humectants.

In one embodiment, the composition of the invention comprising a WIPI-1 agonist may have a pH between about 1 and about 8. In certain embodiments, the pH of the composition will be acidic, i.e., less than 7.0, and in other embodiments will be between about 2 and about 7, in further embodiments will be between about 3.5 and about 5.5.

The invention provides a method for treating aged or aging skin through the topical application of a composition comprising a WIPI-1 agonist, in one embodiment in a cosmetically acceptable vehicle, over the affected area for a period of time sufficient to reduce, ameliorate, reverse or prevent the effects of skin aging.

In some embodiments, the cosmetic compositions can further comprise anti-lipid agents. For example, the cosmetic composition comprising a Carnitine Palmitoyl Transferase-1 (CPT-1) stimulator (e.g. the leaf extract of *Averrhoa carambola*) in an amount effective (or amounts effective) to improve the appearance of skin.

Exemplary anti-cellulite agents include, without limitation, phosphodiesterase inhibitors, such as xanthine analogs, such as caffeine, aminophylline, and theophylline; adenylate cyclase activators, such as forskolin and *Coleus forskohlii* extract; lipolysis stimulators, such as hawthorne extract and cola extract; beta adrenergic receptor agonists, such as isoproterenol; alpha-2-adrenergic antagonists, such as yohimbine and *Ginkgo biloba* extract; perilla oil (see, e.g., U.S. Pat. No. 7,410,658); carnitine and/or creatine (see, e.g., US 2007/0264205 entitled "Cosmetic Composition having Carnitine Creatinate and Methods for Using"). In some embodiments, additional actives may include a collagen stimulator and/or an elastin stimulator, e.g., a substance that stimulates elastin production, and/or a glycosaminoglycan enhancer. Examples of collagen, elastin and glycosaminoglycan enhancers include, e.g., fennel extract, carrot extract, and alfalfa extract. In some embodiments, the additional actives may include a collagenase inhibitor and/or elastase inhibitor.

In some embodiments, the cosmetic compositions can further comprise at least one collagen and/or elastin stimulator. Such collagen or elastin stimulators are effective in, for example, providing improvement in procollagen and/or collagen production and/or improvement in maintenance and remodeling of elastin.

Method of Treating Aging or Aged skin

One embodiment of the current invention relates to a method of modulating WIPI-1 mediated autophagy activity within a skin cell in need thereof by topically applying a WIPI-1 agonist, in one embodiment in a cosmetically suitable vehicle. In a further embodiment, the autophagy activity within the skin cell is increased by at least about 20%, by at least about 40% in one embodiment, and by at least 60% in another embodiment all compared to untreated control and/or autophagy activity of skin cell prior to exposure to WIPI-1 agonist.

The invention further provides a method for treating aging skin by topically applying a composition comprising an extract of WIPI-1 agonist, in one embodiment in a cosmetically acceptable vehicle, over the affected area for a period of time sufficient to reduce, ameliorate, reverse or prevent dermatological signs of aging. This method is particularly useful for treating signs of skin photoaging and intrinsic aging.

Generally, the improvement in the condition and/or aesthetic appearance is selected from the group consisting of: reducing dermatological signs of chronological aging, photo-aging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; preventing, reducing, and/or diminishing the appearance and/or depth of lines and/or wrinkles; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; increasing skin elasticity and/or resiliency; enhancing exfoliation; improving microcirculation; decreasing and/or preventing cellulite formation; and any combinations thereof.

In a further embodiment, the method of the current invention is used to detoxify skin cells in need thereof which may include, but are not limited, cells undergoing or recovering from stress (e.g. free radicals, UV exposure, environmental, and/or chemical); exhibiting reduced protein synthesis and/or autophagy activity; or aged cells.

In a further method, a composition including substituted amino heterocyclic carbamoyl; an extract of *Archidendron clyperia*, an extract of *Ixora chinensis*, an extract of *Maesa japonica*, an extract of *Serrissa japonica*, an extract of *Stephanotis jasminoides*, an extract of *Tiliacora triandra* or any combinations are administered to a melanocyte in need thereof in order to improve a condition related to melanin. This method is particularly useful for treating hypopigmentation resulting from photoaging and intrinsic aging. Generally, the improvement in the condition and/or aesthetic appearance is selected from the group consisting of: increasing melanin production, coloring hypo-pigmented hair, skin, lips and/or nails; evening or optimizing skin discoloration; providing sun-light independent human skin tanning; accelerating tanning in the presence of natural sunlight; darkening, counteracting hypo-pigmentation resulting from administered pharmaceuticals, or repigmenting, hair in-vivo; or preventing gray (depigmented) hair in-vivo.

The composition will typically be applied to the skin, hair, nails, and/or lips, and in a further embodiment to skin, hair, nails and/or lips experiencing reduced autophagy activity, one, two, or three times daily for as long as is necessary to achieve the desired results. The treatment regimen may comprise daily application for at least one week, at least two weeks, at least four weeks, at least eight weeks, or at least twelve weeks. Chronic treatment regimens are also contemplated.

In a specific embodiment, the WIPI-1 agonist is provided in a pharmaceutically, physiologically, cosmetically, and dermatologically-acceptable vehicle, diluent, or carrier, where the composition is topically applied to an affected area of skin and left to remain on the affected area in an amount effective for improving the condition and aesthetic appearance of skin.

A composition comprising a WIPI-1 agonist is topically applied to an "individual in need thereof," by which is meant an individual that stands to benefits from reducing visible signs of skin damage or aging. In a specific embodiment, the WIPI-1 agonist is provided in a pharmaceutically, physiologically, cosmetically, and dermatologically-acceptable vehicle, diluent, or carrier, where the composition is topically applied to an affected area of skin and left to remain on the affected area in an amount effective for improving the condition and aesthetic appearance of skin.

In one embodiment, methods for treating fine lines and wrinkles comprise topically applying the inventive compositions comprising a WIPI-1 agonist to the skin of an individual in need thereof, e.g., topically application directly to the fine line and/or wrinkle in an amount and for a time sufficient to reduce the severity of the fine lines and/or wrinkles or to prevent or inhibit the formation of new fine lines and/or wrinkles. The effect of a composition on the formation or appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin). This embodiment includes treatment of wrinkles on the skin of the hands, arms, legs, neck, chest, and face, including the forehead.

The method of the invention may be employed prophylactically to forestall aging including in patients that have not manifested signs of skin aging, most commonly individuals under 25 years of age. The method may also reverse or treat signs of aging once manifested as is common in patients over 25 years of age.

EXAMPLES

Example 1

Effects of Aging on Autophagy

A. Autophagy Declines with Age in Skin Keratinocytes

Autophagy activity in young versus old primary skin keratinocytes was evaluated using Western blotting. Autophagy was measured by changes in LC3 level, i.e. conversion of LC3-I to the lipidated form LC3-II provides an indicator of autophagy activity (*J Pathol.* 2010 June; 221(2): 117-124). Normal Human Epidermal Keratinocytes (HEK) were obtained from three young donors, average age 23 years, and from three older donors, average age 66 years. The HEKa were maintained in Epilife (Cascade Biologics Inc., MEPI500CA) supplemented with HGSK (Cascade Biologics Inc., S0015) and grown to about 80% confluence. Total protein was obtained from HEKa cells lysed in buffer containing 62.5 mM Tris-HCl (pH6.8), 50 mM DTT, 2% SDS and 10% glycerol. Proteins were then resolved by gel electrophoresis, transferred to Immobilion-P membranes (Millipore IPVH00010), and subjected to immunoblotting with antisera specific for LC3 (Cell Signaling Technology, 4108S), β-actin (Sigma, A1978). The signal was detected with appropriate HRP conjugated secondary antibodies and ECL reagents (Millipore), and quantitated with Image J software (NIH, version 1.38x). The results of an average of 3 independent experiments are summarized in Table 1 below; all values are statistically significant at $p<0.05$. The quantitation of the immunoblot revealed that there is 32% less LC3-II level in older donors compared to the younger donors. Hence, there is a demonstrable decrease in autophagy activity in older donors compared to younger donors.

TABLE 1

Comparison of Autophagy Activity

| Age Group | Autophagy Activity |
|---|---|
| Young (average age 23) | 100% |
| Old (average age 66) | 68% |

B. Autophagy Activity Declines with UV Exposure

The autophagy activity in fibroblast upon UVA exposure and keratinocytes upon exposure to UVB irradiation were evaluated by Western blotting. Normal Human dermal Fibroblasts (HDF) were grown in DMEM (Mediatech; cat. #: 15-013-CV) containing 10% Fetal Bovine Serum (Perbio, SH30070.03), Penicillin/Streptomycin (Mediatech, 30-001-C1), L-Glutamine (Mediatech, 25-005-CI) and Normal Human Epidermal Keratinocytes (HEK) were grown in Epilife (Cascade Biologics Inc., MEPI500CA) supplemented with HGSK (Cascade Biologics Inc., S0015). Cells were then irradiated in phosphate-buffered saline (PBS): HDFa with a dose of 1 $J/cm^2$ UVA and HEK with a dose of 20 $mJ/cm^2$ UVB. UVA and UVB irradiation was performed with UVM-28 EL Series UV Lamp with UVA source emitting at wavelength 365 nm and 305 nm respectively. Fluences were determined with an OPHIR UV meter. 24 hours post-irradiation cells were harvested for protein analysis by Western Blotting (as described above). Quantitation of the immunoblots revealed that there is 60% less autophagy activity in fibroblasts irradiated with UVA and 50% less autophagy activity in keratinocytes irradiated with UVB compared to unirradiated cells, Table 2. Thus, these data indicate that UV exposure leads to a considerable decreased in autophagy activity in both skin fibroblasts and keratinocytes. All values are statistically significant at $p<0.05$.

TABLE 2

Comparison of Autophagy Activity after UV Irradiation

| Treatment | Autophagy Activity |
|---|---|
| Control (Unirradiated) | 100% |
| Fibroblasts (UVA) | 56% (n = 2) |
| Keratinocytes (UVB) | 45.6% (n = 1) |

C. WIPI-1 Decline with UV Exposure

The WIPI-1 levels in skin cells, fibroblast upon UVA exposure and keratinocytes upon exposure to UVB irradiation, were evaluated by Western blotting. Normal Human dermal Fibroblasts (HDF) were grown in DMEM (Mediatech; cat. #: 15-013-CV) containing 10% Fetal Bovine Serum (Perbio, SH30070.03), Penicillin/Streptomycin (Mediatech, 30-001-C1), L-Glutamine (Mediatech, 25-005-CI) and Normal Human Epidermal Keratinocytes (HEK) were grown in Epilife (Cascade Biologics Inc., MEPI500CA) supplemented with HGSK (Cascade Biologics Inc., S0015). Cells were irradiated in phosphate-buffered saline (PBS): HDFa with a dose of 1 J/cm$^2$ UVA and HEK with a dose of 20 mJ/cm$^2$ UVB. UVA and UVB irradiation was performed with UVM-28 EL Series UV Lamp with UVA source emitting at wavelength 365 nm and 305 nm respectively. Fluences were determined with an OPHIR UV meter. 24 hours post-irradiation RNA was isolated using RNeasy RNA extraction kit (74106) from Qiagen. RNA concentrations were then determined using NanoDrop Spectrophotometer ND 1000 (Agilent Technologies).

Reverse transcription reactions were then conducted in a total volume of 20 μl using a High Capacity cDNA kit from AB (PN 4368814). The reverse transcription mixture was prepared to contain 2 μl 10λ TaqMan reverse transcription buffer, 1.2 μl dNTP mix (100 nm), 1.0 μl 10λ Random Hexamer, 1 μl RNase Inhibitor, 1 μl MultiScribe Reverse Transcriptase (50 U/ml), 100 ng of RNA, and RNase-free water to make up the final volume of 20 μl. The reaction was incubated at 25° C. for 10 min, 45° C. for 45 min, and then 95° C. for 5 min in a BIORAD MY CYCLER.

Subsequently, polymerase chain reaction (PCR) was carried out using Applied Biosystems Universal PCR Master Mix (PN 4369016). The mixture contained 10 μl of Taqman Universal PCR mix, 1 μl of primer and probe mix, 2 μl of reverse transcription product, and 7 μl of deionized water. All probes, Taqman assays were, were purchased from Applied Biosystems, Hs00215872_m1 for WIPI-1, and human GAPDH (PN 4352934). The temperature profiles for qPCR were 50° C. for 2 min, and 95° C. for 10 min for 1 cycle, then at 95° C. for 15 sec, and 60° C. for 1 min for 40 cycles carried out in Stratagene Mx 3005P qPCR machine.

Fibroblasts dosed with 1 J/cm2 UVA and keratinocytes with 20 mJ/cm2 UVA were examined by RT-qPCR for expression of levels WIPI-1, using GAPDH as an internal control, 24 hours post-irradiation. WIPI-1 levels in irradiated cells were significantly lower compared to unirradiated cells. Table 3 below shows that there is about 25% less WIPI-1 expression in fibroblasts irradiated with UVA and about 50% less WIPI-1 expression in keratinocytes irradiated with UVB compared to unirradiated cells. Thus, UV exposure leads to a noteworthy decrease in WIPI-1 expression, a critical player in the autophagy activity, in both skin fibroblasts and keratinocytes. All values are statistically significant at $p<0.05$.

TABLE 3

Comparison WIPI-1 Levels in UV irradiated Cells

| Treatment | WIPI-1 Levels |
|---|---|
| Control (Unirradiated) | 100% |
| Fibroblasts (UVA) | 72.7% (n = 3) |
| Keratinocytes (UVB) | 45% (n = 1) |

Example 2

Exemplary HPLC Protocol

Extracts were generally characterized by high performance liquid chromatography. A sample size of approximately 5 mg/mL was dispersed in 25/75 MeOH/H$_2$O and sonicated. The characterization was performed on a Zorbax SBC-18 column (7.5 cm×4.6 mm, 3.5 um particle size) and detection was achieved using diode array UV absorbance, 260 nm 300 nm and 360 nm, with lines on HPLC figures depicted in ascending order and 260 nm on bottom. In one embodiment, the extracted composition of a compound, in substantial isolation, exhibits an HPLC profile substantially similar to that depicted herein.

Operating conditions were flow rate 1.5 ml/min; temperature, 40° C.; sample injection volume, 20 μL, and time of run, 19 minutes. The mobile phase gradient used was as follows:

TABLE 4

Mobile Phase Gradient

| Time | Phase |
|---|---|
| 0 Minutes: | 15% Methanol(Solvent B)/85% Water with 1% acetic acid (Solvent A) |
| 10 Minutes: | 95% Methanol/5% Water with 1% Acetic acid. |
| 15 Minutes: | 15% Methanol/85% Water with1% Acetic acid. |
| 15.01 Minutes: | 95% Methanol/5% Water with1% Acetic acid. |
| 19 Minutes: | 15% Methanol/85% Water with1% Acetic acid |

Example 3

Preparation of Extracts

A. Preparation of *Archidendron clyperia* Extract (Exemplary)

An amount (g) of chopped *Archidendron clyperia* stems and leaves may be gathered and pulverized. Subsequently, reflux extraction, using methods known to those of ordinary skill in the art, may be conducted using 8-10× the weight of the pulverized flowers of water at 100° C. This step may be repeated. The resulting extract may be filtered and condensed using methods known to those of ordinary skill in the art, after which the extract may undergo vacuum distillation at appropriate conditions known to those of ordinary skill in the art. Subsequently, the extract may be mixed with a suitable amount of dextrin and spray dried.

B. Preparation of *Tiliacora triandra* Extract.

*Tiliacora triandra* may be extracted from natural raw materials using methods of aqueous organic solvent extraction as is well known in the art. Two such extraction processes are set forth below.

1. Extraction of *Tiliacora Triandra* by Ethanol

An extract was obtained by extracting the vine of the *Tiliacora triandra* plant using an ethanol extraction scheme. Briefly, the vines of *Tiliacora triandra* Diels were first manually ground into small particles resulting in a powder of about 250 grams per flask (2 flasks). The ground powder was then extracted with 80% ethanol (2×2,000 ml per flask). After filtering and vacuum evaporation, the total concentrated extract was lyophilized resulting in an ethanolic extract of 50 grams. Tannins were removed resulting in an ethanolic extract of *Tiliacora triandra* of 46.04 grams.

2. Extraction of *Tiliacora Triandra* by Hexane

An extract was obtained by extracting the vine of the *Tiliacora triandra* plant using a hexane extraction scheme. Briefly, the vines of the *Tiliacora triandra* were first manually ground into small particles resulting in a powder of about 250 grams per flask (2 flasks). The ground powder was then extracted with 100% hexane (2×2,000 ml per flask). After filtering and vacuum evaporation, the total concentrated extract was dried by hot air oven at 40° C. resulting in an hexanolic extract of *Tiliacora triandra* of 0.61 grams.

As noted in the remaining specification, modifications and adaptations of this extraction process are possible, particularly during a scale-up to larger volumes for production.

Figure 2:
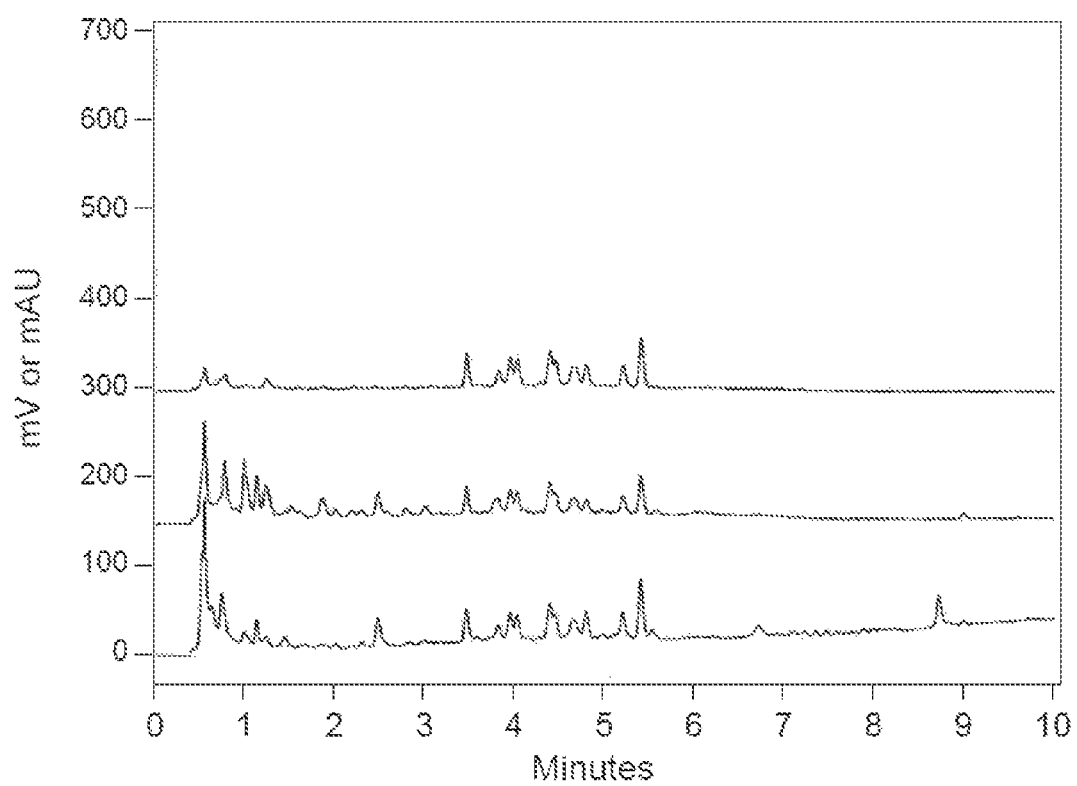
FIG. 2 is a HPLC profile of an extract of *Tiliacora triandra*

A representative HPLC trace of a *Tiliacora triandra* aqueous extraction is depicted in FIG. 2.

C. Preparation of *Ixora* chinensis

Preparation of *Ixora chinensis* extract is generally described in U.S. patent application Ser. No. 13/158,947, filed on Jun. 30, 2010, the entirety of which is incorporated by reference for all purposes and U.S. patent application Ser. No. 13/324,150, filed on Dec. 13, 2011, the entirety of which is incorporated by reference for all purposes. An extract is obtained by extracting the dry chopped plant of *Ixora chinensis* Lamk. using an ethanol extraction followed by a further extraction with hexane. Briefly, the chopped plant of *Ixora chinensis* is first manually ground into small particles resulting in a powder of about 250 grams. The ground powder is then extracted with 50% ethanol. After filtering and vacuum evaporation, the total concentrated extract is diluted with water, centrifuged and filtered. The liquid is then thrice extracted with hexane, the hexane upper layer being discarded and the aqueous layer being lyophilized resulting in an extract of about 90 grams.

Figure 3:
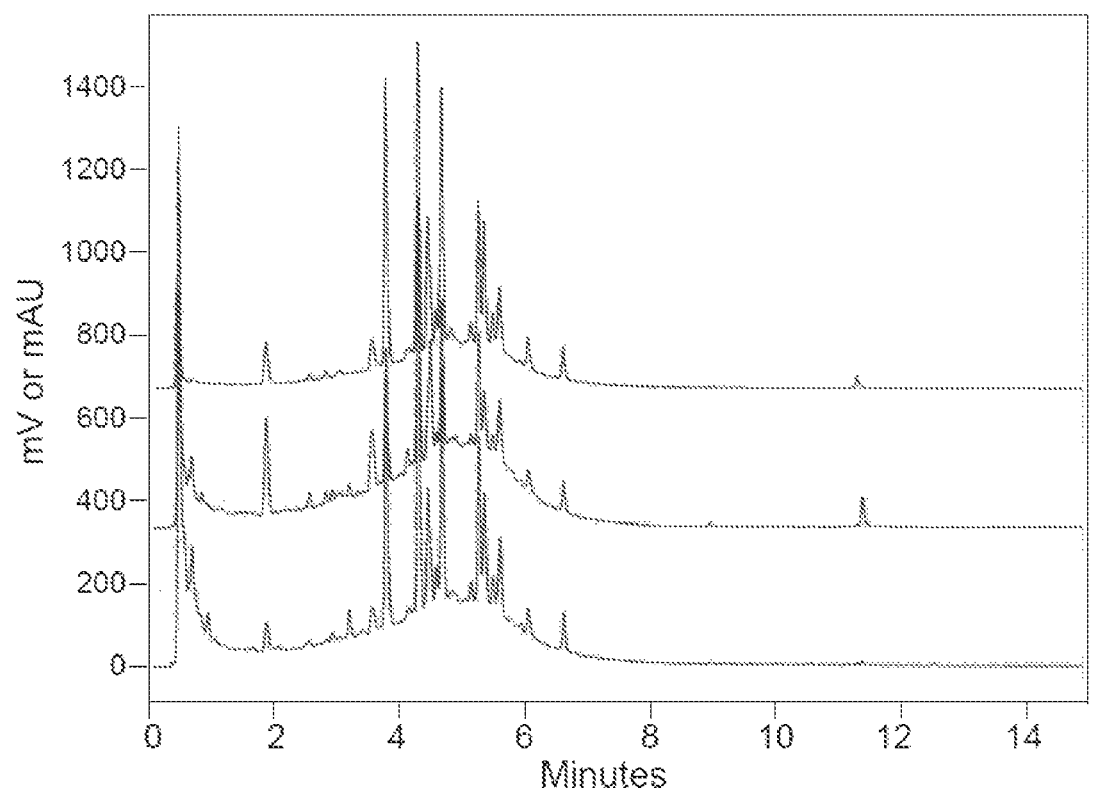
FIG. 3 is a HPLC profile of an extract of *Ixora chinensis*

A HPLC trace of a representative *Ixora chinensis* extract is found at FIG. 3.

D. Preparation of *Serisa japonica*

Preparation of *Serrisa japonica* extract is generally described in PCT Patent Application Serial No. PCT/US12/68858 filed on Dec. 11, 2012 with Qian Zheng as lead inventor, the entirety of which is incorporated by reference herein for all purposes.

250 g of dried and powdered material derived from the leaves and/or stems of *Serissa japonica* was percolated with 1000 ml EtOH/$H_2O$ (50:50, v/v) at room temperature for 24 hours. This percolation was repeated 2 times and then the EtOH/$H_2O$ extraction solution was concentrated under vacuum by rotary evaporator at 40-50° C. to 150 ml or end of distillation, whichever occurs first.

The concentrated solution was then diluted with pure water to 1500 ml of volume and sonicated for 20 minutes to generate an aqueous suspension. The suspension was left to stand at 4° C. for 12 h and then centrifuged. The supernatant was then transferred to a separation funnel where three separate extraction were done with 500 ml of hexane each. The hexane solvent was recycled, and the hexane extract was discarded.

Charcoal (10% by w. vs. total dry matter content) was then added to the aqueous phase yielded from the hexane extraction and stirred for 1 hour. The solution was then filtered and concentrated under vacuum at 40-50° C. to adjust the concentration of solution to 5% (w/v) of its dry matter. The adjusted solution was then passed through a Diaion HP-20 column (20 times of the dry weight) and washed successively with:

1) H20: 2 times Diaion HP-20 column volume (100 g HP-20 is equal to 210 ml of column volume);

2) 20% aqueous EtOH: 2 times Diaion HP-20 column volume;

3) 50% aqueous EtOH: 2 times Diaion HP-20 column volume;

4) 95% aqueous EtOH: 3 times Diaion HP-20 column volume.

The eluents of washes 1-4 were concentrated, respectively, to dryness to obtain fractions 1-4.

As noted in the remaining specification, modifications and adaptations of this extraction process are possible, particularly during a scale-up to larger volumes for production.

Figure 4:
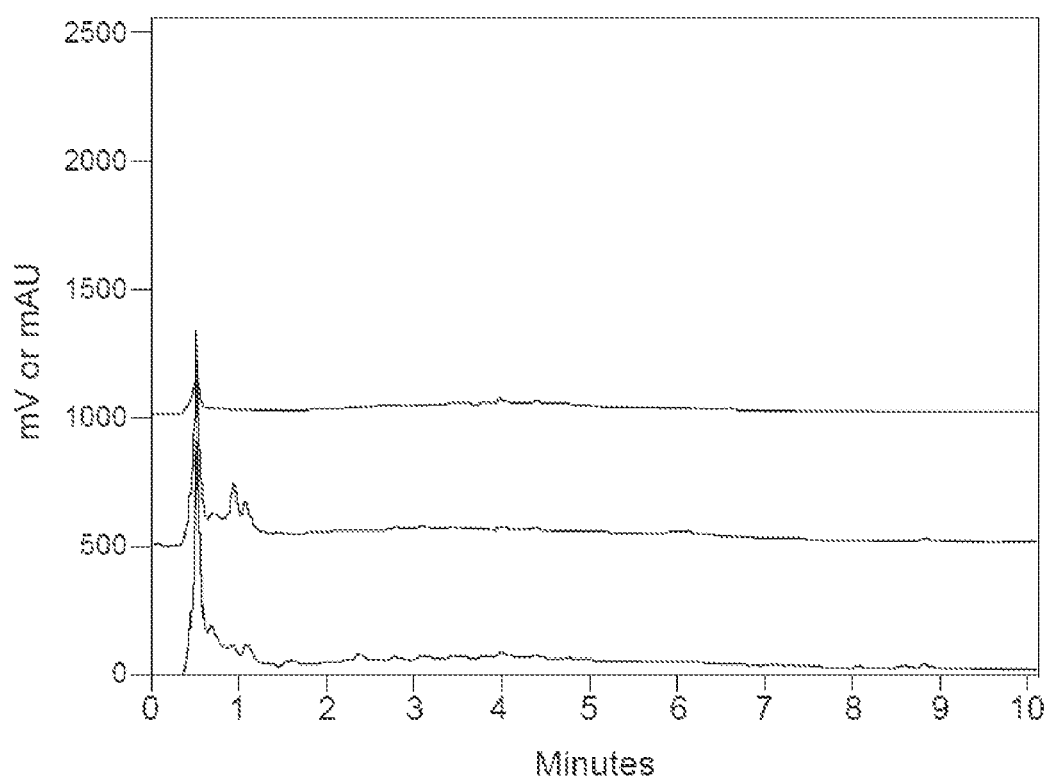
FIG. 4 is a HPLC profile of an extract of *Serisa japonica*

A HPLC trace of a representative *Serissa japonica* extract is found at FIG. 4.

E. Preparation of *Maesa japonica*

Preparation of *Maesa japonica* extract is generally described in U.S. patent application Ser. No. 13/710,585 filed on Dec. 11, 2012 with Siming Chen as lead inventor, the entirety of which is incorporated by reference herein for all purposes.

250 g of chopped *Maesa japonica* flowers were gathered and then dried in an electric oven at 60° C. for 2 or 3 days. The dried flowers were then added to 1 L of 50% hydroethanol (EtOHI$H_2O$ 50-50 v/v; 3×4 volume) in a container and extraction occurred by shaking the container at 150 rpm at 37° C. for 12 h. This extraction was repeated three times to achieve 3 L of total extract. The total extract was then subjected to vacuum concentration using a rotary evaporator at a temperature of 40-50° C. until the volume was reduced to about 150 m. The concentrated fraction was then diluted with pure water to 1500 ml and was left to stand at 4° C. for 12 h (or more) and then centrifuged to remove any residue. The 1500 ml of the now clarified solution was treated, twice, with 750 ml of hexane in a separation funnel and the organic layer was discarded. The dry content of the remaining aqueous homogenous solution was confirmed by taking a 150 ml sample of the homogenous solution and lyophilizing the sample. The resulting powder was weighed and used to calculate the total amount of dry matter in the homogenous solution. The resulting powder was then re-dissolved in water (about 100-150 ml) and pooled with the homogenous solution. 10% by weight of charcoal was then added to the homogenous solution, about 17 g of charcoal for a solution of about 1500 ml. The solution was then stirred at 50° C. for 1 hour and then then filtered on a filter paper (type, manufacturer) and the step was repeated. Next, the now clear solution is fractioned by liquid/liquid extraction with water saturated n-butanol. The saturated butanol was prepared by adding to butanol with the same volume of water in a separating funnel, after mixing the organic upper layer was collected and used for the liquid/liquid of clear solution. About 2250 ml of the water saturated butanol was prepared for the 1500 ml clear solution. The water saturated butanol was divided into three 750 ml portions and each was used to treat the clear solution three times in a separatory funnel. The resulting organic layer (butanolic extract) and aqueous layers from each run through the separatory funnel were collected and pooled separately. First, an equal volume of water was added to the pooled butanolic extract and the solution was concentrated in a rotary evaporator under vacuum. When the distillation stopped an equal volume of water was added and the concentration was repeated. The concentration was repeated a third time and the resulting solution was lyophilized (first purified extract). Second, the aqueous layer resulting from each run through the separatory funnel was concentrated by rotary evaporator under vacuum to remove butanol (azeotrope boiling point is less than 100° C., bath temperature 60° C.). When distillation stopped, the aqueous solution was lyphylized (second purified extract). The first and second extracts were then combined and weighed.

Extraction Protocol 2 (Exemplary)

An amount (g) of chopped *Maesa japonica* flowers may be gathered and pulverized. Subsequently, reflux extraction, using methods known to those of ordinary skill in the art, may be conducted using 8-10× the weight of the pulverized flowers of water at 100° C. This step may be repeated. The resulting extract may be filtered and condensed using methods known to those of ordinary skill in the art, after which the extract may undergo vacuum distillation at appropriate conditions known to those of ordinary skill in the art. Subsequently, the extract may be mixed with a suitable amount of dextrin and spray dried.

Figure 5:
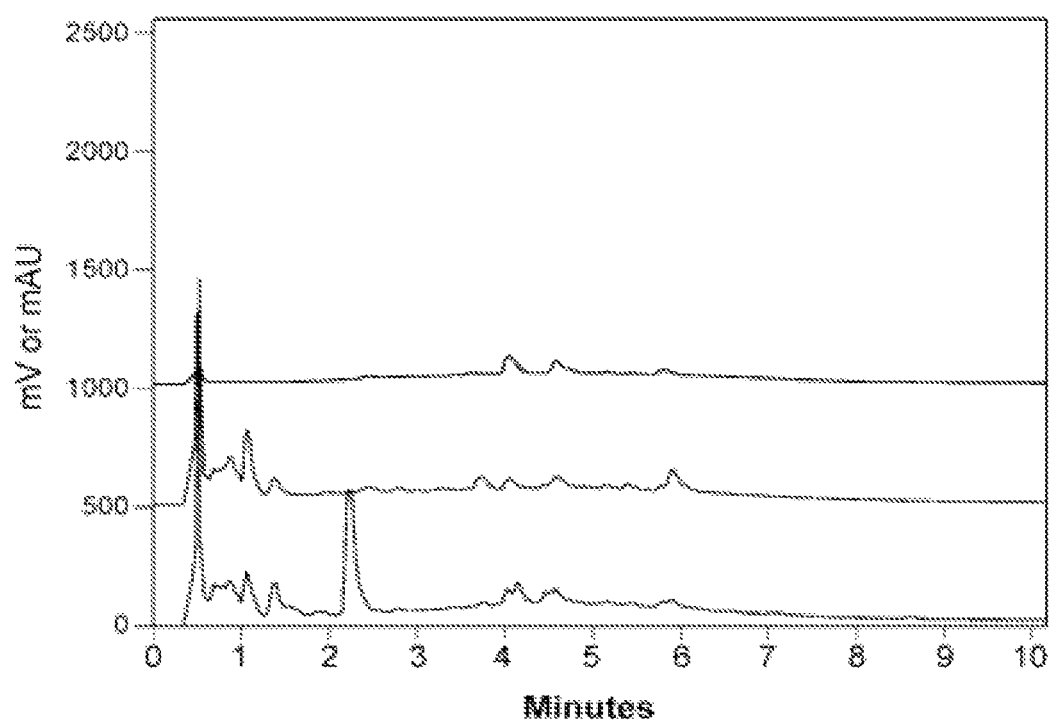
FIG. 5 is a HPLC profile of an extract of *Maesa japonica*

A HPLC trace of a representative *Medemia nobilis* extract is found at FIG. 5.

F. Preparation of *Stephanotis jasminoides* Tissue Culture

Preparation of *Stephanotis jasminoides* extract is generally described in PCT Patent Application Serial No. PCT/US12/68866 filed on Dec. 11, 2012 with Raaj Khusial as lead inventor, the entirety of which is incorporated by reference herein for all purposes.

The meristem of *Stephanotis jasminoides* was excised and transferred to solid medium and propagated. The resulting callus is grown to a specific mass and then transferred to liquid medium in a bioreactor where the cells were grown under desired conditions until a desired density was achieved. The cell culture was then homogenized and filtered to remove any solids. The resulting extract was lyophilized.

As noted in the remaining specification, modifications and adaptations of this cell culture/extraction process are possible, particularly during a scale-up to larger volumes for production.

Figure 6:
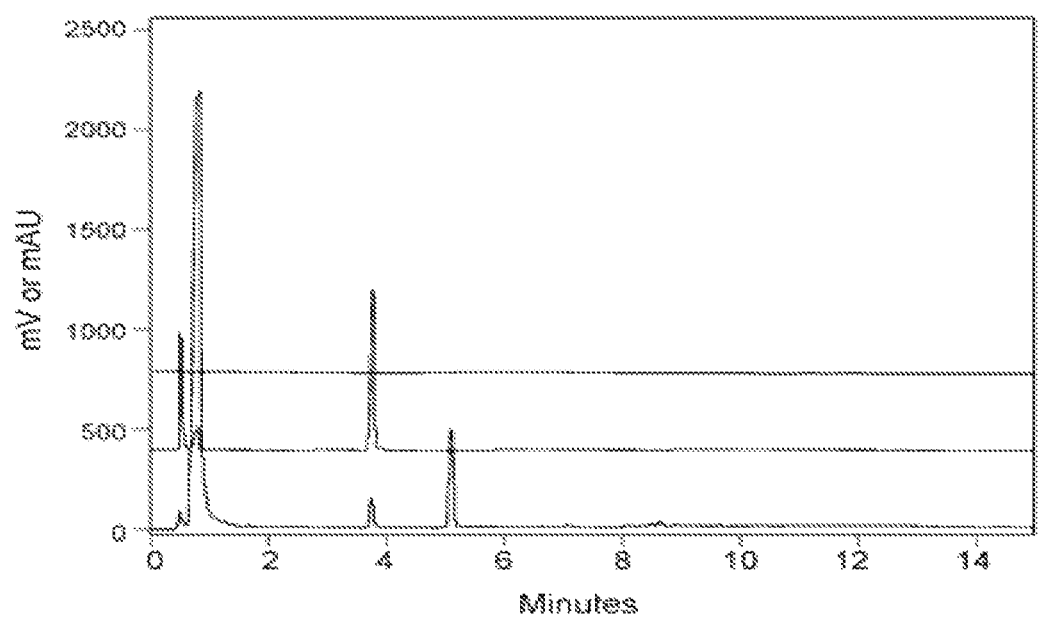
FIG. 6 is a HPLC profile of an extract of *Stephanotis jasminoides*

A HPLC trace of a representative *Stephanotis jasminoides* extract is found at FIG. 6.

Example 4

WIPI-1 Screening

A variety of botanical extract and synthetic compounds were tested for the ability to up-regulate WIPI-1. Normal human dermal fibroblasts or keratinocytes were cultured in 96-well tissue culture treated plates, containing appropriate culture medium. Stock solutions of actives were made in an appropriate vehicle (water/Ethanol/DMSO). Cells were treated with test material or respective vehicle control diluted in growth medium for 24 hours in a humidified 37° C. incubator with 10% $CO_2$. The concentrations of each extract are provided based on the dry weight of the given plant extract, by which is meant the weight of the extract after volatile extraction solvents have been removed. After incubation, growth medium from each plate was removed and 100 µL of lysis buffer was added to the wells and placed in 37° C. incubator with 10% $CO_2$ for 30 minutes. At the end of incubation, the cells were collected in freezer plates and placed in −80° C. freezer, until analysis. Changes in mRNA after treatment were analysed using Panomics Quantigene multiplex assay that employs a branched DNA technology, following manufacturer's instructions (Affymetrix, CA). Percent increase (up-regulation) in mRNA for the WIPI-1 were calculated by comparing the test results to the control. The percent up-regulation is converted to a scaled score: 0: 0-20%; +: 21-40%; ++: 41-60%; +++: 61-80%; ++++: >80%.

TABLE 6

| WIPI-1 Screening | | | |
|---|---|---|---|
| Product/Ingredient Name | Concentration | HDFa Activity Level | HEKa Activity Level |
| *Serrissa japonica* | 0.1% | + | |
| *Maesa joponica* | 0.01% | + | |
| *Maesa joponica* | 0.1% | ++++ | |
| *Tiliacora triandra* | 0.1% | +++ | |
| Analog 1 | 0.01% | | + |
| Analog 1 | 0.001% | | + |
| *Stephanotis jasminoides* | 0.01% | | + |
| *Archidendron clyperia* | 0.1% | | + |
| *Ixora chinensis* | 0.01% | | + |

As shown in Table 5 above, each of the prospective WIPI-1 agonists were found to upregulate WIPI-1 within either fibroblasts or keratinocytes. In particular, WIPI-1 in fibroblasts was upregulated by *Serissa Japonica*, *Maesa japonica*, and *Tiliacora triandra*. The 0.1% concentration of both *Maesa japonica* and *Tiliacora triandra* led to greater than 60% upregulation in WIPI-1. Analog 1, *Stephanotis jasminodes*, *Archidendron clyperia*, and *Ixora chinensis* upregulated WIPI-1 within keratinocytes.

Example 4

Exemplary Compositions

A. Exemplary Anti-Cellulite Compositions

Cosmetic compositions comprising a WIPI-1 agonist for topical application to skin exhibiting or at risk of exhibiting signs of aging are provided in Table 7.

TABLE 7

| Sample Anti-Cellulite Cosmetic Composition Ingredient |
|---|
| Aesthetic modifier |
| Emollient |
| Emulsifier |
| Anti-inflammation agent |
| Chelater |
| Coolant |
| Elastin stimulator |
| Exfoliator |
| Fragrance |
| Humectant |
| Microcirculation enhancer |
| Neutralizer |
| Preservative |
| Sunscreen |
| Collagenase/elastinase inhibitor |
| Hawthorne (*Crataeg. monog.*) Fruit. Extract |
| Coffee Seed Extract |
| Soybean (*Glycine soja*) Extract |
| *Celosia cristata* Extract & *Prunella vulgaris* Extract |
| L-Carnitine Hydrochloride |
| *Averrhoa carambola* Leaf Extract |
| WIPI-1 Agonist |
| Demineralized water |

B. Exemplary Anti-Aging Facial Cosmetic Composition

Cosmetic compositions comprising a WIPI-1 agonist for topical application to areas of the face exhibiting or at risk of exhibiting signs of aging due to a reduction in the quality of autophagy activity are provided in Table 8.

TABLE 8

Sample Anti-aging Facial Cosmetic Composition
Ingredient

Aesthetic modifier
Emollient
Emulsifier
Anti-inflammation agent
Chelater
Coolant
Elastin stimulator
Exfoliator
Fragrance
Humectant
Microcirculation enhancer
Neutralizer
Preservative
Sunscreen
Collagenase/elastinase inhibitor
Phytol
Antioxidant
Fennel Extract
Carrot extract
Pomegranate extract
Thiodipropionic acid (TDPA)
Green tea polyphenol
L-4 Thiazolylanine
WIPI-1 Agonist
Demineralized water These anti-aging compositions are believed to be effective to treat, reverse, ameliorate and/or prevent signs of aging, specifically, the compositions are believed to reduce the appearance of wrinkles, lines, and sagging in the skin. The compositions of Tables 7 and 8 are applied to skin in need of treatment, by which is meant skin in need of an anti-aging benefit. The cosmetic compositions may be applied directly to the skin in need of treatment.

These cosmetic compositions are applied to aged skin, two or three times daily for as long as is necessary to achieve desired anti-aging or skin lightening results, a treatment regimen which may comprise daily application for at least one week, at least two weeks, at least four weeks, at least eight weeks, or at least twelve weeks. Alternatively, the exemplary cosmetic compositions may be used in chronic treatment of aged or discolored skin.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

We hereby claim:

1. A method of treating the skin comprising topically applying to an area of the skin a composition comprising a cosmetically acceptable vehicle and an active agent that up-regulates WIPI-1, wherein said active agent is selected from the group consisting of:

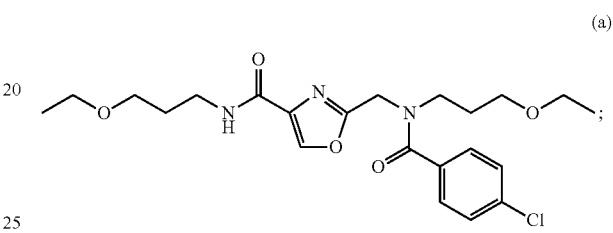

(a)

(b) an extract of *Archidendron clypearia;*
(c) an extract of *Maesa japonica;*
(d) an extract of *Serissa japonica;* and
(e) an extract of *Stephanotis jasminoides.*

2. The method of claim 1, wherein the active agent that up-regulates WIPI-1 is an extract of *Archidendron clypearia.*

3. The method of claim 1, wherein the active agent that up-regulates WIPI-1 is an extract of *Maesa japonica.*

4. The method of claim 1, wherein the active agent that up-regulates WIPI-1 is an extract of *Serissa japonica.*

5. The method of claim 1, wherein the active agent that up-regulates WIPI-1 is an extract of *Stephanotis jasminoides.*

* * * * *